US011464878B2

United States Patent
Santin et al.

(10) Patent No.: US 11,464,878 B2
(45) Date of Patent: Oct. 11, 2022

(54) BIOSPECIFIC AGENTS FOR BONE

(71) Applicant: ORTHOPAEDIC RESEARCH UK, London (GB)

(72) Inventors: Matteo Santin, Brighton (GB); Steven Thomas Meikle, Eastborne (GB); Lubinda Mbundi, Senanga (ZM)

(73) Assignee: ORTHOPAEDIC RESEARCH UK, London (GB)

( * ) Notice: Subject to any disclaimer, the term of this patent is extended or adjusted under 35 U.S.C. 154(b) by 102 days.

(21) Appl. No.: 16/693,780

(22) Filed: Nov. 25, 2019

(65) Prior Publication Data

US 2020/0215207 A1 Jul. 9, 2020

Related U.S. Application Data

(63) Continuation of application No. 14/765,508, filed as application No. PCT/GB2014/050265 on Jan. 31, 2014, now abandoned.

(30) Foreign Application Priority Data

Feb. 7, 2013 (GB) ...................... 1302199

(51) Int. Cl.
| | |
|---|---|
| A61B 5/055 | (2006.01) |
| A61K 49/14 | (2006.01) |
| A61K 49/18 | (2006.01) |
| A61K 49/04 | (2006.01) |
| B82Y 5/00 | (2011.01) |
| A61K 47/69 | (2017.01) |
| A61B 6/03 | (2006.01) |
| A61K 38/17 | (2006.01) |
| G01R 33/56 | (2006.01) |
| A61P 19/08 | (2006.01) |

(52) U.S. Cl.
CPC .............. *A61K 49/14* (2013.01); *A61B 6/032* (2013.01); *A61K 38/1793* (2013.01); *A61K 47/6929* (2017.08); *A61K 49/0428* (2013.01); *A61K 49/1875* (2013.01); *B82Y 5/00* (2013.01); *G01R 33/5601* (2013.01); *A61K 49/1866* (2013.01); *A61P 19/08* (2018.01)

(58) Field of Classification Search
None
See application file for complete search history.

(56) References Cited

U.S. PATENT DOCUMENTS

| | | | |
|---|---|---|---|
| 7,323,542 B2 | 1/2008 | Balian | |
| 2005/0175584 A1* | 8/2005 | Paciotti | ................... A61P 35/00 424/85.2 |
| 2008/0206146 A1 | 8/2008 | Akhtari et al. | |
| 2013/0095499 A1* | 4/2013 | Rose-Petruck | .... A61K 49/0428 435/7.1 |

FOREIGN PATENT DOCUMENTS

| | | |
|---|---|---|
| AU | 2012204100 | 8/2012 |
| WO | 2002/007792 | 1/2002 |
| WO | 2006102377 | 9/2006 |

OTHER PUBLICATIONS

Lee et al. (Biochem. 2010, 49, 1364-1376).*
Aoki, K., et al., "Peptide-based delivery to bone", Advanced Drug Delivery Reviews, 2012, pp. 1220-1238, vol. 64.
Fanord, F., et al., "Bisphosphonate-modified gold nanoparticles: a useful vehicle to study the treatment of osteonecrosis of the femoral head", Nanotechnology, 2011, pp. 1-11, 035102, vol. 22.
Gong, Y., et al., "LDL Receptor-Related Protein 5 (LRP5) Affects Bone Accrual and Eye Development", Cell, Nov. 16, 2001, pp. 513-523, vol. 107.
Huang, C.-C., et al., "Enhancing Transversal Relaxation for Magnetite Nanoparticles in MR Imaging Using Gd3+-Chelated Mesoporous Silica Shells", ACSNano, 2011, pp. 3905-3916, vol. 5, No. 5.
Tan, M., et al., "MR Molecular Imaging of Prostate Cancer with a Peptide-Targeted Contrast Agent in a Mouse Orthotopic Prostate Cancer Model", Pharm. Res., 2012, pp. 953-960, vol. 29.
Wang, T., et al., "Targeted Cell Uptake of a Noninternalizing Antibody Through Conjugation to Iron Oxide Nanoparticles in Primary Central Nervous System Lymphoma", Peer-Review Reports, World Neurosurgery, Jan. 5, 2013, pp. 134-141, vol. 80, No. 1.
Zhang et al. "Preparation of functionalized gold nanoparticles as a targeted X-ray contrast agent for damaged bone tissue", Nanoscale, vol. 2, No. 4, pp. 582-586, 2010.

(Continued)

*Primary Examiner* — Michael G. Hartley
*Assistant Examiner* — Melissa J Perreira
(74) *Attorney, Agent, or Firm* — Gates & Cooper LLP

(57) ABSTRACT

A bone biospecific agent comprises a contrast material core, which is visible using Magnetic Resonance Imaging (MRI) or Computed Tomography (CT). The contrast material core is surrounded by a polymeric shell, which is functionalised with a bone-targeting peptide. In use, the peptide targets the biospecific agent to bone. The bone biospecific agent can be used in diagnostic imaging techniques, such as MRI and CT, and in imaging bone remodelling activities, detecting and treating pathological bone conditions and/or bone repair processes. The invention extends to the diagnosis and/or treatment of bone disease and bone pathologies using the biospecific agents.

16 Claims, 20 Drawing Sheets

Specification includes a Sequence Listing.

(56) References Cited

OTHER PUBLICATIONS

Lalatonne et al. "Superparamagnetic Bifunctional Bisphosphonates Nanoparticles: A Potential MRI Contrast Agent for Osteoporosis Therapy and Diagnostic", Journal of Osteoporosis, vol. 140, No. 10, pp. 4382-4387, 2010.
PCT International Search Report and Written Opinion for PCT/GB2014/050265 dated Jun. 13, 2014.
Cheng et al. (J. Biol. Chem. 2004, 279, 8269-8277).
Ta et al. PNAS 2010, 20281-20286.
Heath et al. (Cancer Res. 2007, 67, 202-208).

* cited by examiner

A

B

C

D

BIOSPECIFIC AGENTS FOR BONE

CROSS-REFERENCE TO RELATED APPLICATIONS

This application is a continuation application that claims the benefit of U.S. patent application Ser. No. 14/765,508, filed Aug. 3, 2015, which is the National Stage of International Application No. PCT/GB2014/050265 (International Publication No. WO2014/122431), filed Jan. 31, 2014, which claims priority to UK Patent Application Serial No. 1302199.3, filed Feb. 7, 2013, the contents of which are incorporated herein by reference.

The present invention relates to biospecific agents for bone, and in particular to bone biospecific agents, including nanoparticles, sub-micron particles and atomic or molecular elements, which are functionalised with peptides that are specific for bone. The invention is especially concerned with the use of these bone biospecific agents in diagnostic imaging techniques, such as Magnetic Resonance Imaging (MRI) and Computed Tomography (CT), and the use of the agents in imaging bone remodelling activities, detecting and treating pathological bone conditions and/or bone repair processes. The invention extends to the diagnosis and/or treatment of bone disease and bone pathologies using the biospecific agents.

Magnetic Resonance Imaging (MRI) and Computed Tomography (CT) are the methods of choice in the imaging of tissues. MRI is based on the ability of large magnetic fields to produce a net magnetic vector temporarily changing the alignment of the protons in the highly hydrated tissues. MRI is mainly suited for the imaging of injuries in ligaments, tendons and spinal cord as well as of brain tumours. However, the technique does not allow imaging of the bony tissues as detailed as those that can be obtained by CT.

CT is based on X-ray attenuation which is detected by a detector where the value of pixels is calculated and then transformed into an image. Quantitative computed tomography (QCT) is able to provide measurements of bone density, and measures the true volumetric (mg/cm$^3$) in three dimensions, as opposed to the two dimensional area of bone density. This enables the operator to distinguish between cortical and cancellous bone and accurately determine skeletal changes over time. As a result, QCT is employed principally for vertebral body cancellous bone density examination. QCT can selectively assess the metabolically active and structurally important trabecular bone and discriminate between vertebral fractures and measure bone loss. However, QCT is very expensive and exposes patients to higher doses of ionising radiation when compared to Dual-energy E-ray absorptiometry (DXA).

Contrast agents are indispensable to the improvement of imaging in both techniques as they enhance the image definition. Contrast agents with no specificity for tissues are currently used in MRI, which are based on either iron oxide nanoparticles or gadolinium. However, although providing good imaging and safety for the patients, these contrast agents are unable to recognise specific tissues and cell types. Furthermore, current CT contrast agents, such as iodine-based compounds have several limitations, including short imaging times due to rapid renal clearance, renal toxicity, and vascular permeation.

Although the pathogenesis of osteoporosis is unclear, data suggests that it is caused by an imbalance between the bone resorption activities of the osteoclasts and the bone forming activities of the osteoblasts. This imbalanced cellular activity leads to a progressive weakening of the bony tissue leading to the formation of micro-fractures that are at the origin of clinically-significant fractures. Epidemiological studies have demonstrated that these fractures tend to occur in specific anatomical sites, including vertebral bodies, sub-throcanteric femoural bone and the wrists. Although the imbalanced cellular activity plays a critical role in most osteoporotic cases, its relative contribution to bone loss (i.e. osteopenia) may vary depending on a number of different factors including age, gender, genetic predisposition to osteoporosis, lack of exercise, medication, health and nutrition. Generally, osteoporosis is classed as either primary (i.e. senile) or secondary (i.e. non-age related).

Primary osteoporosis is further categorised as either type I (i.e. post-menopausal) or type II (i.e. age-related). Type I osteoporosis occurs mainly at the age of 50 to 70 largely due to oestrogen loss at menopause and affects the trabecular bone. Type II is directly related to the aging process and usually occurs at the age of 70 and above, affecting both trabecular and cortical bone. However, it is well-known that changes in bone density occur in every person regardless of age. During normal growth, bone formation is faster than bone loss, up until the age of 30-35 when the peak bone mass (PBM) is reached. Once PBM is reached, both men and women begin to lose bone at the rate of 0.5-2% per year with considerable individual variation. In women, menopause further accelerates the rate of bone loss for about to years.

Secondary osteoporosis results from either a complication of underlying medical conditions or lifestyle (e.g. alcohol consumption, drug abuse or poor diet) and can affect people of all ages. Indeed, infants with lower than expected bone density in the early weeks of life have been reported to develop osteoporosis. Medical conditions that can cause secondary osteoporosis include hormone imbalances, rheumatoid arthritis, liver failure, kidney failure, impaired gastrointestinal function, multiple sclerosis, scurvy, anorexia nervosa and athlete triad. In some cases, it is not the condition that causes osteoporosis, but the drugs used. Medication such as corticosteroids, some hormones, and lithium to manage medical conditions have been linked with the development of secondary osteoporosis. Generally, osteoporosis is of more clinical significance in women than in men.

Osteosarcoma is the most common primary sarcoma (incidence: 0.2-3/100 000/year) characterised by osteoblastic differentiation leading to production of poorly organised osteoid or bone growth that affects bone integrity. Although osteosarcomas can also be malignant, its absolute incidence among malignant tumors is low. Within strict histological definition, osteosarcoma lesions are considerably diverse in histological features and grade and its prognosis is dependent not only on these parameters, but also on its anatomic site. Another feature of osteosarcomas is the tendency to produce variable amounts of cartilage matrix and fibrous tissue which in some cases predominates the actual production of bone. As a result, there are three subtype classifications, namely osteoblastic, chondroblastic and fribroblastic osteosarcoma.

Within the skeletal system, osteosarcomas usually develop in the metaphysis of a long extremity bone, most commonly around the knee and its presence in the axial skeleton or craniofacial bones is widely observed in adults. With regard to bone, osteosacorma may develop inside the bones (in the intramedullary or intracortical compartment), on the surfaces of bones, and in extraosseous sites.

Bone metastases are characterised by osteoblastic, osteolytic or both osteoblastic and osteolytic phenotypes. Different malignancies exhibit osteotropism and higher affinity for bone with carcinomas being the most common metastatic deposits in bone. Common malignancies that end up in bone include breast, prostate and lung cancers. Thus, being widely considered a significant challenge in the field of oncology. Once in bone, metastatic cells increase osteoblastic proliferation and activity, including an increase in the expression and release of RANKL through the release of soluble mediators or via cell-to-cell contact. This then activates the differentiation of pre-osteoclast and activity of mature osteoclasts through the RANKL-RANK interaction. Bone resorption by osteoclasts releases cytokines and other growth factors such as TGF-β and insulin like growth factor (IGF) necessary for the tumour cell, thereby enhancing tumour growth and perpetuating the process. Increased bone resorption leaves behind osteolytic lesions which are detectable by X-ray, densitometric techniques and MRI. Osteoblastic metastases abnormally increased bone formation and are seen as dense areas of bone on X-Rays, and MRI.

The frequency of bone resorption activation varies more between health and diseased bone than the differences between bone resorption and formation phases. The frequency of bone activation is characterised by the amount of the so-called bone multi-cellular units (BMU) on the surface of bone, which is greater in osteoporotic bone than in normal bone and is associated with increased osteoclast and resorption lacunae in the skeleton. Histological stain on bone biopsies in a systemic disease, such as osteoporosis, may be used as diagnosis, and the stain would make it possible to microscopically localise solid particulate materials used for diagnosis and treatment (i.e. Prussian blue stain for iron).

In the view of above, it will be appreciated that there is a growing need to provide novel means for diagnosing and/or treating bone-related diseases.

Thus, according to a first aspect of the invention, there is provided a bone biospecific agent comprising a contrast material core, which is visible using Magnetic Resonance Imaging (MRI) or Computed Tomography (CT), the contrast material core being surrounded by a polymeric shell, which is functionalised with a bone-targeting peptide, wherein the peptide, in use, targets the biospecific agent to bone.

The bone biospecific agent of the present invention is based upon the design, development and improvement of a range of different nanoparticles, submicron particles and atomic or molecular elements, which are described in detail below, and their uses in either MRI or CT imaging techniques. The bone biospecific agent comprises a core comprising a conventional contrast material, which has been functionalised with a peptide that can specifically recognise a bone cell (e.g. an osteoblast or an osteoclast) or mineralized bone extracellular matrix (e.g. hydroxyapatite). Hence, the peptide renders the agent specific for biorecognition in bone pathologies. As described in Examples 1-3, and as illustrated in FIG. 5E, the inventors have prepared a series of different bone-specific agents in which a range of different bone-targeting peptides have been used to functionalise a polymeric shell.

Careful selection of the material used for the contrast material in the core, of the polymer forming the polymeric shell, and also of the bone-specific functionalising peptide enables the bone biospecific agents to be used in either diagnosis and/or therapy of various bone-related conditions. Therefore, the biospecific agent may be used in imaging bone remodelling activities, detecting pathological conditions (e.g. bone resorption or bone tumours) and/or tissue repair processes following fractures or to surgical intervention. Advantageously, the biospecific agents of the invention have been designed to specifically interact with the elements of diseased bone that are essential for bone remodelling, and can be carefully tailored into injectable materials for less invasive early diagnosis and/or treatment of bone diseases.

Preferably, the contrast material forms or constitutes the inner core of the biospecific agents of the invention surrounded by an outer polymeric shell. The mean diameter of the contrast material core may be between 5 nm and 30 nm, or between 10 nm and 20 nm.

The contrast material core, which is visible using MRI or CT, may comprise a metallic or non-metallic material. The contrast material core may comprise a magnetic or non-magnetic material. In embodiments where the contrast material is magnetic, it may comprise an MRI contrast material. The contrast material may comprise a paramagnetic or superparamagnetic material. For example, the contrast material core may comprise iron, nickel, cobalt or dysprosium or a compound, such as an oxide or alloy, which contains one or more of these elements. Preferably, the contrast material comprises magnetite ($Fe_3O_4$).

In embodiments wherein the contrast material is non-magnetic, it may comprise both a MRI and a CT contrast material. For example, the contrast material core may comprise gadolinium, gold, iodine or boro-sulphate. Each of these materials may be used as either MRI or as CT contrast materials. Preferably, the contrast material comprises gadolinium.

The polymeric shell of the bone biospecific agent may comprise a polymer, which may comprise a polypeptide, a charged protein, a polysaccharide or a nucleic acid. Suitable polymers may comprise any biocompatible natural or synthetic polymer including, but not limited to, chitosan, collagen, gelatine, hyaluronic acid, poly(ethylene glycol) poly(lactic acid), poly(glycolic acid), poly(epsilon-caprolactone) and poly(acrylic acid). A preferred polymer for the polymeric shell may comprise chitosan. Chitosan is known to be a linear polysaccharide comprising randomly distributed β-(1-4)-linked D-glucosamine (deacetyleated unit) and N-acetyl-D-glucosamine (acetylated unit).

The polymeric shell is attached to the contrast material core by physical absorption or by covalent bonding, depending on the chemistry of the polymer and of the surface of the contrast material core. It may be desirable to derivatise the polymeric shell in order to enable its efficient functionalisation with the bone-targeting peptide. For example, the polymeric shell may be derivatised by reacting the polymer with succinic anhydride. This can be carried out in order to provide a spacer between the polymer and the bone-targeting peptide, which would reduce steric hindrance. It may also improve the solubility of the polymer used (e.g. chitosan) and physiological pH. Succinic anhydride is also known as dihydro-2,5-furandione and has the molecular formula $C_4H_4O_3$. Methods by which the polymer, for example, chitosan, may be derivatised by succinic anhydride will be known to the skilled person, and are described in Example 1.

The amount of bone-targeting peptide that is attached to the polymeric shell depends on the amount of functional groups, type of polymer used and chemistry of attachment. Preferably, the peptides are arranged in a spaced-apart array covering the outer surface of the polymeric shell. The polymeric shell may be functionalised with one species (i.e. the same sequence) of bone-targeting peptide, which targets the biospecific agent to bone. However, the shell may be functionalised with two or more species (i.e. having different sequences) of bone-targeting peptide.

For example, the bone-targeting peptide may target the biospecific agent to a cell present exclusively in bone, for example an osteoblast, osteocyte, osteoclast, bone cell progenitor, osteoclast progenitor or a bone lining cell. Preferably, the bone-targeting peptide targets the biospecific agent to osteoblasts or osteoclasts. Peptides with sequences able to mimic GAP-junction communication (e.g. connexin 43, cx43) which are specific to inter and intra osteoblast and osteoclast cell-to-cell communication may also be used as the bone-targeting peptide. In addition, the bone-targeting peptide can direct the biospecific agent to the bone mineral phase; i.e. hydroxyapatite. Biospecific agents comprising hydroxyapatite-targeting peptides are therefore a valuable tool for monitoring the mineralization of a forming bony tissue following a traumatic event or during the progression of diseases, such as osteoporosis.

It is known that many human bone disorders associated with deregulated bone remodelling cycle, such as Paget's disease, and cancerous bone metastases, are indicative of an imbalance between osteoprogeterin (OPG) and RANKL. The inventors therefore believe that the RANK-RANKL-OPG pathway and associated pathways may be exploited to develop cost-effective, biospecific materials for the treatment and diagnosis of metabolic bone diseases.

Thus, the bone-targeting peptide may be associated with the Gap junction intercellular communication (GJIC) and the RANK-RANKL-OPG triad pathways. The fact that the biospecific agent of the invention is specific for RANK-RANKL means that it would identify and target the cell within the specimen. In diseases such as osteosarcoma and bone metastases, the tumour may be localised with X-RAY and MRI, and the biospecific agent may enhance the signal and improve resolution which may allow the visualisation of smaller lesions that may otherwise be missed.

The bone-targeting peptide may comprise an amino acid sequence that mimics OPG by binding RANK such that RANKL-induced osteoclast differentiation and activity is reduced or prevented. Alternatively, the bone targeting peptide may be able to mimic proteins such as Connexin 43 participating in the inhibition of osteoclast-osteoclast and or osteoclast-osteoblast interactions. Bone-targeting peptides can also be used that recognise migrating osteoblasts or the mineral phase of bone (i.e. hydroxyapatite). Therefore, the bone-targeting peptide may comprise one of the following amino acid sequences:
  (a) SRPTEKTIFII (SEQ ID No.1). This peptide is derived from Connexin 43 mimetic peptide (Cx43) Gap27, and may be used to block osteoclast-osteoclast and/or osteoclast-osteoblast interaction. This peptide is designated GAP27p when referred to herein. It is a known sequence and inhibits osteoblast-osteoclast contact dependent sell communication.
  (b) YCLEIEFCY (SEQ ID No.2). This peptide is based on OPG residual 113-122 (this represents the amino acid sequence in the OPG peptide, and is derived from a segment of the protein identified by the amino acids 113-122) and specifically binds to RANK and inhibits RANKL-induced osteoclast differentiation and activity. This peptide is designated OP3-1 when referred to herein.
  (c) YCEIEFCYLIR (SEQ ID No.3). This peptide is also based on OPG residual 113-122, and specifically binds to RANK and inhibit RANKL-induced osteoclast differentiation and activity. This peptide is designated OP3-4 when referred to herein.
  (d) FHRRIKA (SEQ ID No.4). This peptide specifically binds to osteoblasts facilitating their migration.
  (e) PSHRN (SEQ ID No.5). This peptide also specifically binds to osteoblasts.
  (f) YIGSR (SEQ ID No.6). This peptide specifically binds to bone endothelial cells.
  (g) STLPIPHEFSRE (SEQ ID No.7). This peptide has high affinity for hydroxyapatite.
  (h) VTKHLNQISQSY (SEQ ID No.8). This peptide also has high affinity for hydroxyapatite.

The inventors have found that, in some embodiments, it may be preferred to use a connecting or spacer peptide for connecting the bone-targeting peptide to the polymeric shell, and preferably a derivatised form thereof (for example, with succinic). Such connecting peptides exhibit improved solubility in aqueous solution, and therefore facilitate the grafting step of the peptide to the agent, and later improve presentation of the bioligand to the cell.

In one embodiment, a suitable connecting peptide which may be used may comprise the amino acid sequence K—(KK). This peptide is designated SEQ ID No.9 or G1PL when referred to herein. This peptide is a polar molecule and hence improves solubility and accessibility.

In another embodiment, a connecting peptide may comprise the amino acid sequence K—(KK)—(KKKK). This peptide is designated SEQ ID No.10 or G2PL when referred to herein.

In yet another embodiment, a connecting peptide may comprise the amino acid sequence K-(KK)-(KKKK)-(KKKKKKKK). This peptide is designated SEQ ID No.11 or G3PL when referred to herein.

Thus, the bone-targeting peptide may comprise any of SEQ ID No.9-11, or a functional variant or fragment thereof. For example, any of the peptides designated SEQ ID No.1-8 may be conjugated to any of SEQ ID No.9-11. Accordingly, in another embodiment, the bone-targeting peptide may comprise the following amino acid sequence, or a functional fragment or variant thereof:
  (i) (KKKK)-(KK)-K-YCLEIEFCY (SEQ ID No.12). This peptide comprises the OP3-1 peptide (i.e. SEQ ID No.2) tethered to the connecting peptide G2PL (i.e. SEQ ID No.10). This peptide is designated G2PL-OP3-1 when referred to herein.

The inventors have also demonstrated that the bone-targeting peptide may comprise 1,4,7,10-tetraazacyclododecane-1,4,7,10-tetraacetic acid (i.e. DOTA). It comprises gadoteric acid, a macrocycle-structured Gd-based MRI contrast agent, consisting of the organic acid "DOTA" as a chelating agent. Accordingly, in another embodiment, the bone-targeting peptide may comprise the following amino acid sequence, or a functional fragment or variant thereof:
  (j) DOTA-KGG-YCLEIEFCYLIR (SEQ ID No.13). This peptide is a novel DOTA-tethered OP3-4 peptide for the chelation of MRI visible $Gd^{3+}$. This peptide is designated DOTA-OP3-4 when referred to herein.
  (k) DOTA-Gd-KGG-YCLEIEFCYLIR (SEQ ID No.14). This peptide is a novel MRI-detectable OP3-4 derivative with $Gd^{3+}$ chelate. This peptide is designated DOTA-Gd-OP3-4 when referred to herein.
  (l) DOTA-Gd-FHRRIKA (SEQ ID No.15). This peptide is a novel MRI-detectable osteoblast migration derivative with a $Gd^{3+}$ chelate. This peptide is designated DOTA-Gd-FHRRIKA when referred to herein.

The DOTA molecule is fairly large, very acidic and reactive, and so this molecule may need the user of a spacer or connecting peptide to avoid compromising the potency of the bone-targeting peptide.

As described in the Examples, the bone-targeting peptide may be synthesised by known methods, for example solid phase peptide synthesis (SPPS) using the conventional 9-fluorenylmethyloxy carbonyl (Fmoc) protection/deprotection strategy.

The bone-targeting peptide may be cyclised. The cyclised form is more chemically stable and others have reported improved activity (See Shin J et al 2008), example by dimethyl sulfoxide (DMSO) oxidation to form cysteine-cysteine disulfide bonds.

The bone-targeting peptide may be attached to the polymeric shell of the bone biospecific agent by covalent bonding. Preferably, the polymeric shell comprises chitosan, which may be derivatised, for example using succinic anhydride. In an embodiment, the peptides may be covalently attached to the polymeric shell using carbodiimide chemistry in order to create the nanoparticles of the invention.

The biospecific agent may comprise a bioactive compound, which may be delivered to the bone due to the presence of the bone-targeting peptide. For example, the bioactive compound may be selected from a group of molecules consisting of: a dye, electrochemical mediator, protein, peptide, chemical compound (such as a drug), genetic material (such as an oligonucleotide, DNA, RNA), small molecule, antibody, enzyme, and other bioactive molecule. The bioactive compound may be conjugated to the biospecific agent, for example by encapsulation during cross-linking, adsorption, ionotropic interaction or direct covalent attachment of the polymer coating.

In one embodiment, the bone biospecific agent may comprise a nanoparticle. In another embodiment, the bone biospecific agent may comprise a sub-micron particle. The nanoparticle may be substantially spherical in shape.

The mean diameter of the biospecific agent may be sub-micron, i.e. less than 1000 nm. The mean diameter of the biospecific agent may be 100-450 nm.

The biospecific agent may be produced by initially carrying out a step of ionotropic cross-linking, followed by dissolving the polymer and cross-linker at predetermined concentrations. The inner contrast material core may be added to the mix. The polymer may be dissolved in a solution comprising the cross-linker (for example, drop-wise under continuous stirring). The mixture may be allowed to react (e.g. for at least 30 minutes). The mixture may then be centrifuged and the resultant particles (i.e. the biospecific agent) collected in a suitable solvent (e.g. ethanol or water). The particles may be freeze-dried for storage and/or characterised. A connecting peptide (or spacer) may be added, for example by carrying out a ring opening reaction, for example in the case of succinic anhydride. Finally, the bone-targeting peptide may be attached, for example using carbodiimide chemistry.

As described in Example 4, the inventors have demonstrated that the biospecific agents of the invention can be effectively used in MRI or CT imaging techniques depending on the material of contrast agent that is used.

Therefore, according to a second aspect, there is provided the bone biospecific agent according to the first aspect, for use in diagnosis.

It will be appreciated that the bone biospecific agent may be used as a biosensor in a range of different biological imaging applications. For example, the biospecific agent is preferably used in MRI or CT imaging techniques, as a biolabel.

Thus, in a third aspect, there is provided use of the bone biospecific agent of the first aspect, as an MRI biolabel or as a CT biolabel.

In a fourth aspect, there is provided a biolabel comprising the bone biospecific agent according to the first aspect.

The biolabel may be used in MRI or CT imaging.

In a fifth aspect, there is provided an MRI or CT imaging method comprising the use of the bone biospecific agent of the first aspect.

The inventors have demonstrated that the bone biospecific agent can be used in imaging bone remodelling activities, detecting pathological bone conditions (e.g. bone resorption, bone tumours, osteoporosis etc.) and/or bone tissue repair processes following fractures. Furthermore, in addition to the various imaging techniques that can harness the powerful bone-targeting properties of the bone specific agent, Example also explains how the biospecific agents of the invention can be effectively used to inhibit osteoclastogenesis and osteoclast activity, and therefore prevent bone resorption. The inventors therefore believe that the biospecific agent can be used in a variety of therapeutic applications for treating bone disease.

Therefore, according to a sixth aspect, there is provided the bone biospecific agent according to the first aspect, for use in therapy, and preferably as a medicament.

The bone biospecific agent of the invention is particularly useful for preventing or treating bone disease.

Hence, according to a seventh aspect, there is provided the bone biospecific agent according to the first aspect, for use in treating, preventing or ameliorating bone disease.

In an eighth aspect, there is provided a method of treating, ameliorating or preventing bone disease, the method comprising administering, to a subject in need of such treatment, a therapeutically effective amount of a bone biospecific agent according to the first aspect.

Examples of bone disease which may be treated include bone resorption, treatment of bone tumour, Paget's disease, rheumatoid arthritis, osteoarthritis, osteoporosis, osteosarcoma, osteopenia and bone metastases, including osteolytic and osteoblastic phenotypes etc.

It will be appreciated that a bone biospecific agent of the present invention may be used in a medicament, which may be used in a monotherapy. Alternatively, agents according to the invention may be used as an adjunct to, or in combination among them or in combination with, known therapies for treating bone disease.

A biospecific agent of the present invention may be combined in compositions having a number of different forms depending, in particular, on the manner in which the composition is to be used. Thus, for example, the composition may be in the form of a powder, powder suspension, tablet, capsule, liquid, gel, hydrogel, aerosol, spray, micellar solution, or any other suitable form that may be administered to a person or animal in need of treatment. It will be appreciated that the vehicle of medicaments according to the invention should be one which is well-tolerated by the subject to whom it is given.

Medicaments comprising biospecific agents of the present invention may be used in a number of ways. For instance, oral administration may be required, in which case the biospecific agent may be contained within a composition that may, for example, be ingested orally in the form of a tablet, capsule or liquid. Compositions comprising biospecific agents of the present invention may be administered by inhalation (e.g. intranasally).

A bioactive agent of the present invention may also be incorporated within a slow- or delayed-release device. The device may be located at least adjacent the treatment site. Such devices may be particularly advantageous when long-term treatment with a biospecific agent of the present invention is required and which would normally require frequent administration (e.g. at least daily injection).

In a preferred embodiment, a biospecific agent of the present invention and compositions according to the invention may be administered to a subject by injection into the blood stream or directly into a site requiring treatment, i.e. the bone. Injections may be intravenous (bolus or infusion) or subcutaneous (bolus or infusion), or intradermal (bolus or infusion) or intraosseus.

It will be appreciated that the amount of biospecific agent of the present invention that is required is determined by its biological activity and bioavailability, which in turn depends on the mode of administration, the physico-chemical properties of the agent and whether it is being used as a monotherapy or in a combined therapy. The frequency of administration will also be influenced by the half-life of the agent within the subject being treated. Optimal dosages to be administered may be determined by those skilled in the art, and will vary with the particular agent in use, the strength of the pharmaceutical composition, the mode of administration, and the advancement of the disease being diagnosed or treated. Additional factors depending on the particular subject being treated will result in a need to adjust dosages, including subject age, weight, gender, diet, and time of administration.

Generally, a daily dose of between 0.01 µg/kg of body weight and 0.5 g/kg of body weight of the biospecific agent may be used for treating, ameliorating, or preventing bone disease.

The agent of the present invention may be administered before, during or after onset of disease. Daily doses may be given as a single administration (e.g. a single daily injection). Alternatively, the agent may require administration twice or more times during a day. As an example, the agent may be administered as two (or more depending upon the severity of the bone disease being treated) daily doses of between 25 mg and 7000 mg (i.e. assuming a body weight of 70 kg). A patient receiving treatment may take a first dose upon waking and then a second dose in the evening (if on a two dose regime) or at 3- or 4-hourly intervals thereafter. Alternatively, a slow release device may be used to provide optimal doses of agent to a patient without the need to administer repeated doses.

Known procedures, such as those conventionally employed by the pharmaceutical industry (e.g. in vivo experimentation, clinical trials, etc.), may be used to form specific formulations comprising a biospecific agent and precise therapeutic regimes (such as daily doses of the agent and the frequency of administration).

Hence, in a ninth aspect of the invention, there is provided a pharmaceutical composition, comprising the bone biospecific agent according to the first aspect, and a pharmaceutically acceptable vehicle.

The invention also provides in a tenth aspect, a process for making the composition according to the ninth aspect, the process comprising contacting a therapeutically effective amount of the bone biospecific agent according to the first aspect, and a pharmaceutically acceptable vehicle.

A "subject" may be a vertebrate, mammal, or domestic animal. Hence, compositions and medicaments according to the invention may be used to treat any mammal, for example livestock (e.g. a horse), pets, or may be used in other veterinary applications. Most preferably, however, the subject is a human being.

A "therapeutically effective amount" of the biospecific agent is any amount which, when administered to a subject, is the amount of medicament or drug that is needed to treat a bone disease, or produce the desired effect. For example, the therapeutically effective amount of agent used may be from about 0.01 mg to about 800 mg.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. The vehicle may also be an encapsulating material. In powders, the vehicle is a finely divided solid that is in admixture with the finely divided active agents according to the invention. In tablets, the active agent (e.g. the biospecific agent) may be mixed with a vehicle having the necessary compression properties in suitable proportions and compacted in the shape and size desired. The powders and tablets preferably contain up to 99% of the capsule or cell. Suitable solid vehicles include, for example calcium phosphate, magnesium stearate, talc, sugars, lactose, dextrin, starch, gelatine, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The agent of the present invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil).

For parenteral administration, the vehicle can also be an oily ester such as ethyl oleate and isopropyl myristate. Sterile liquid vehicles are useful in sterile liquid form compositions for parenteral administration.

Liquid pharmaceutical compositions, which are sterile solutions or suspensions, can be utilized by, for example, intramuscular, intrathecal, epidural, intraperitoneal, intravenous and particularly subcutaneous injection. The agent may be prepared as a sterile solid composition that may be dissolved or suspended at the time of administration using sterile water, saline, or other appropriate sterile injectable medium.

The biospecific agent and pharmaceutical compositions of the invention may be administered orally in the form of a sterile solution or suspension containing other solutes or suspending agents (for example, enough saline or glucose to make the solution isotonic), bile salts, acacia, gelatine, sorbitan monoleate, polysorbate 80 (oleate esters of sorbitol and its anhydrides copolymerized with ethylene oxide) and the like. The biospecific agent according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which:—

Figure 13:
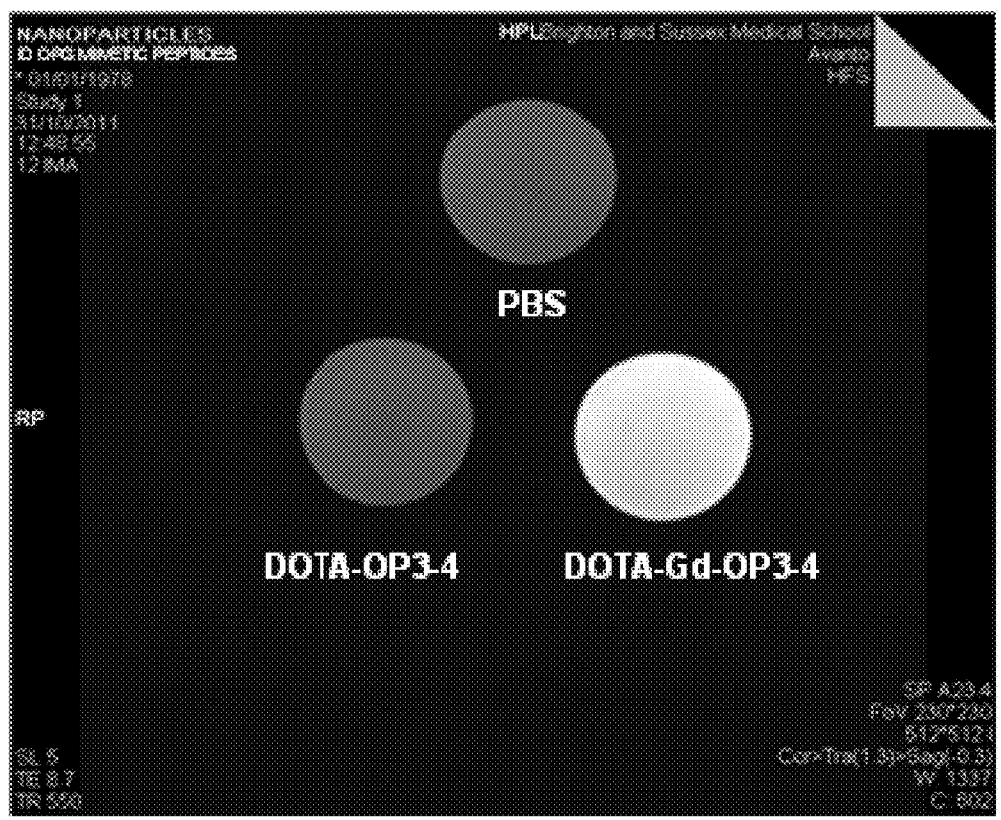
Figure 14:
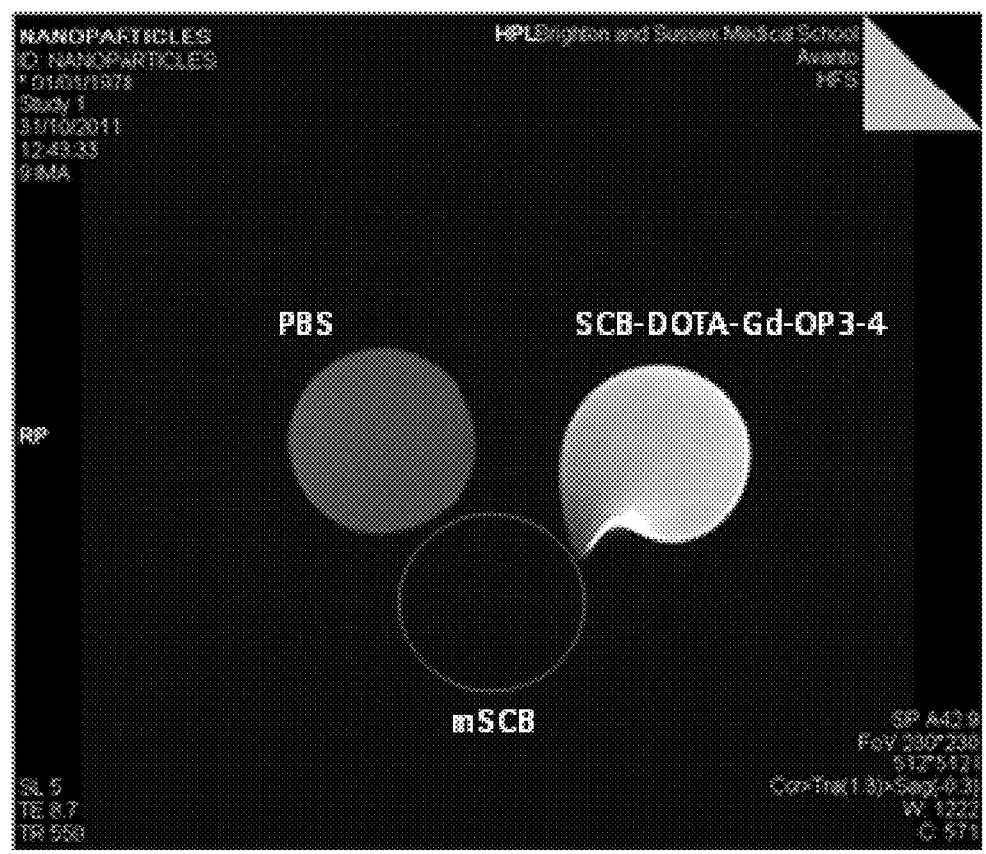
Figure 15:
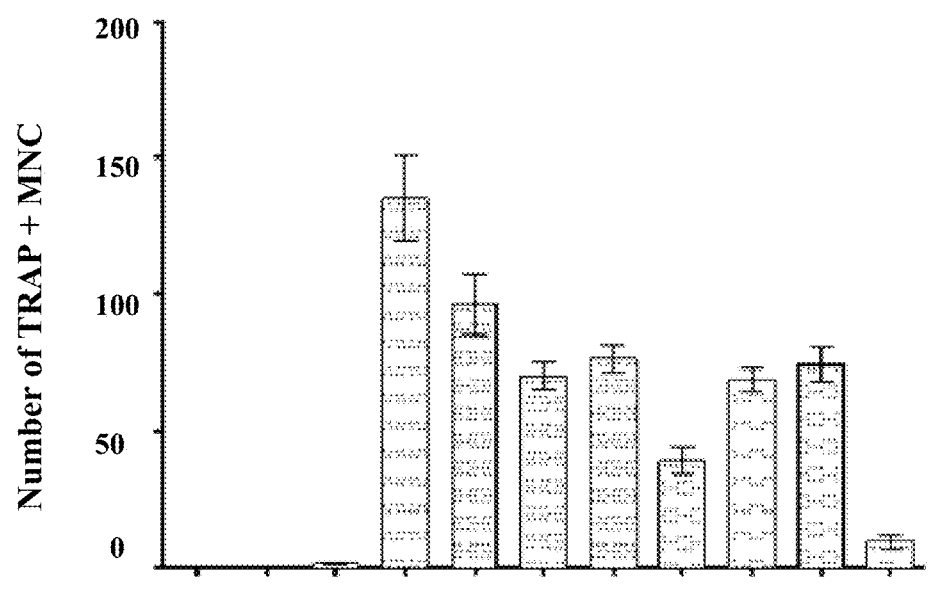
Figure 16:
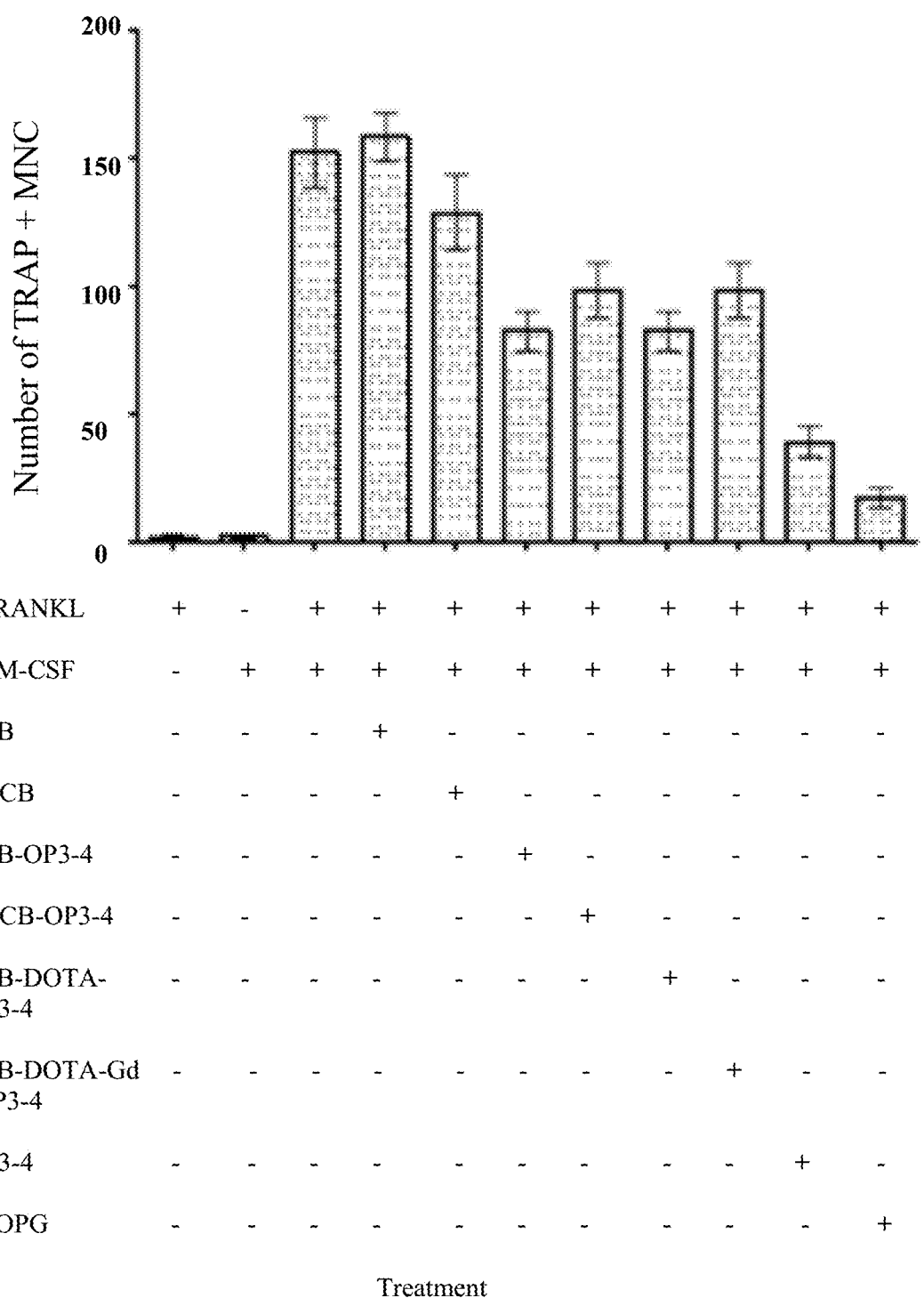
Figure 17:
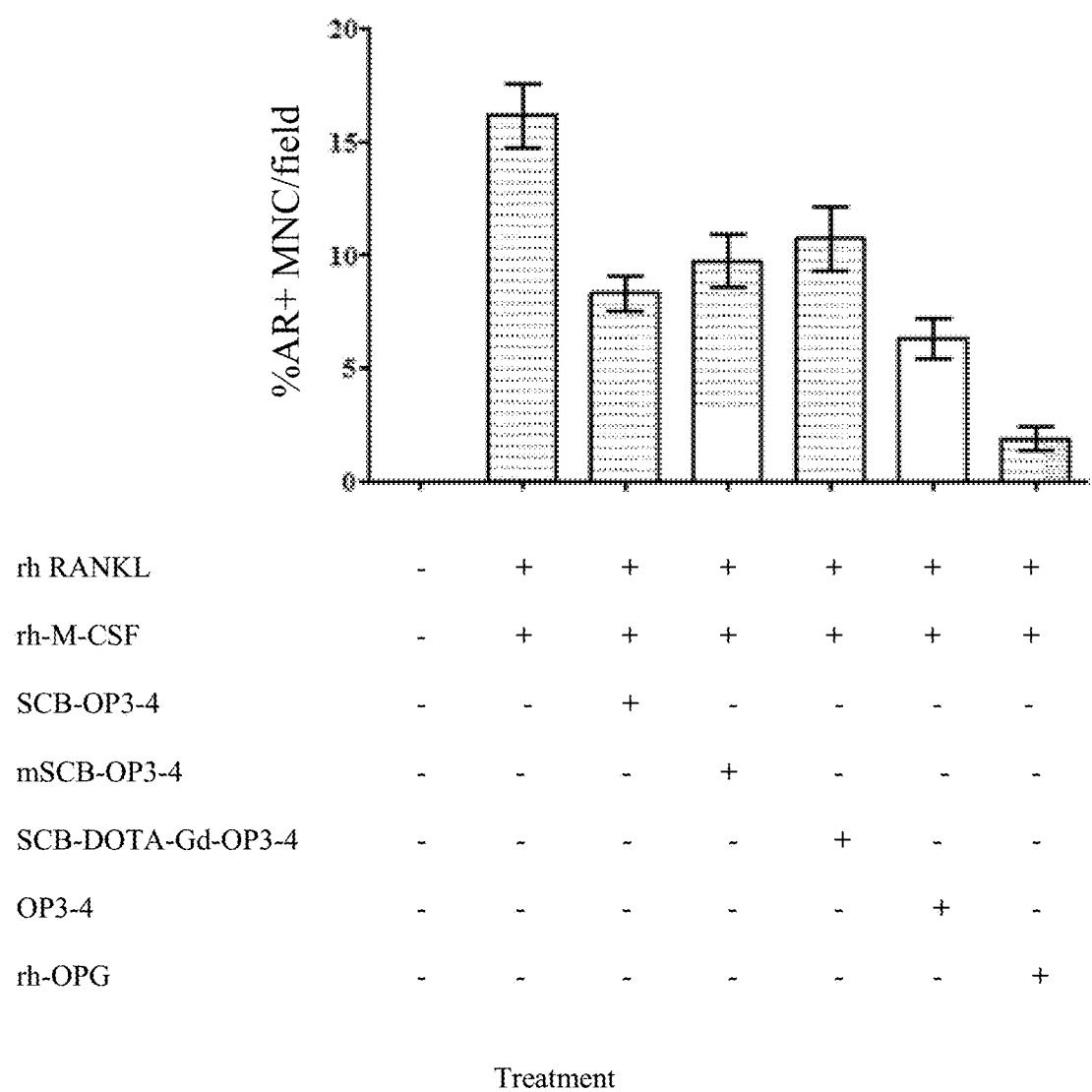
Figure 18:
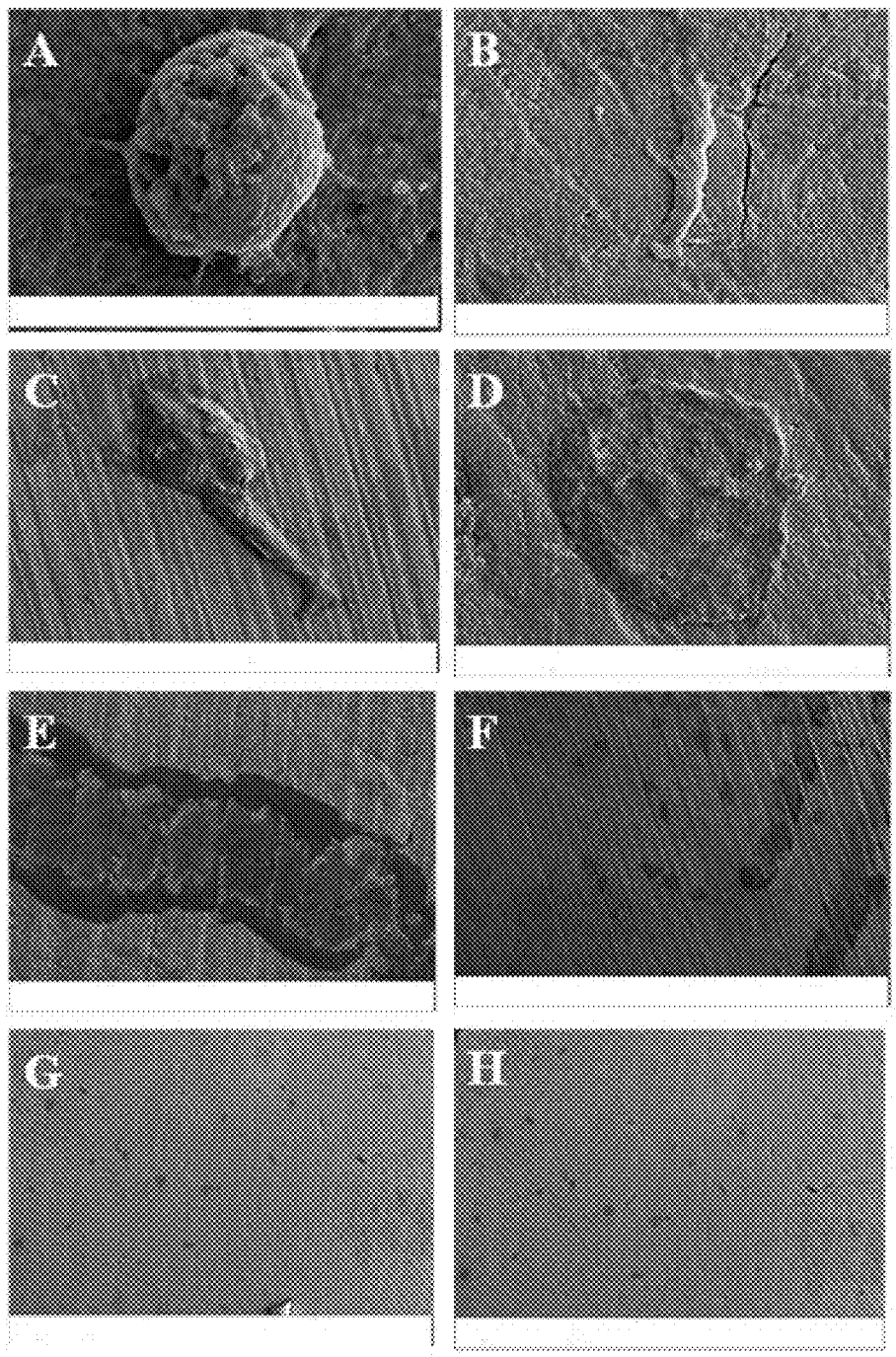

FIG. 13 shows MRI analysis of DOTA-Gd-OP3-4 conjugate and the negative controls DOTA-OP3-4 conjugate and PBS. The peptides were dissolved in PBS at a concentration of 0.4 µg/ml. The scans were performed in the T1-weighted mode with TE 8.7 and TR 550;

FIG. 14 shows an MRI analysis of magnetic nanoparticle-OP3-4 conjugate (mSCB) and nanoparticle-DOTA-Gd-OP3-4 conjugate at 0.4 µg/ml. Phosphate buffered saline (PBS) was used as a negative control. Gadolinium-based and magnetic beads-based contrast agents provide the typical bright and dark imaging respectively;

FIG. 15 shows the effect of peptides on rh RANKL-induced osteoclastogenesis. Monocytes were cultured for 6 days in αMEM medium supplemented with peptides at concentration of 100 µM. The concentration of rh RANKL was 500 ng/ml, of rh M-CSF was 25 ng/ml and rh OPG was 500 ng/ml. The culture medium with respective dosages was replaced after 3 days;

FIG. 16 shows the effect of peptide-tethered nanoparticle on rh RANKL-induced osteoclastogenesis. Monocytes were cultured for 6 days in αMEM medium supplemented with peptides (100 µM) and beads (25 µg/ml). The concentration of rh RANKL was 500 ng/ml, of rh M-CSF was 25 ng/ml and rh OPG was 500 ng/ml. The culture medium with the respective dosages was replaced after 3 days;

FIG. 17 shows the inhibition of rh RANKL-induced osteoclast activity in a monocyte monoculture as determined by analysis of F-actin ring formation using rhodamine-phalloidin and Hoescht 33258 dual stain; and FIG. 18 are representative SEM micrographs of cells cultured on bone slices. (A) untreated cells (B) M-CSF only (C-D) M-CSF+rh RANK (E-F) representative resorption lacunae (G-H) cells treated with OP3-4 peptide and tethered contrast agents.

EXAMPLES

Figures 5A, 5B:
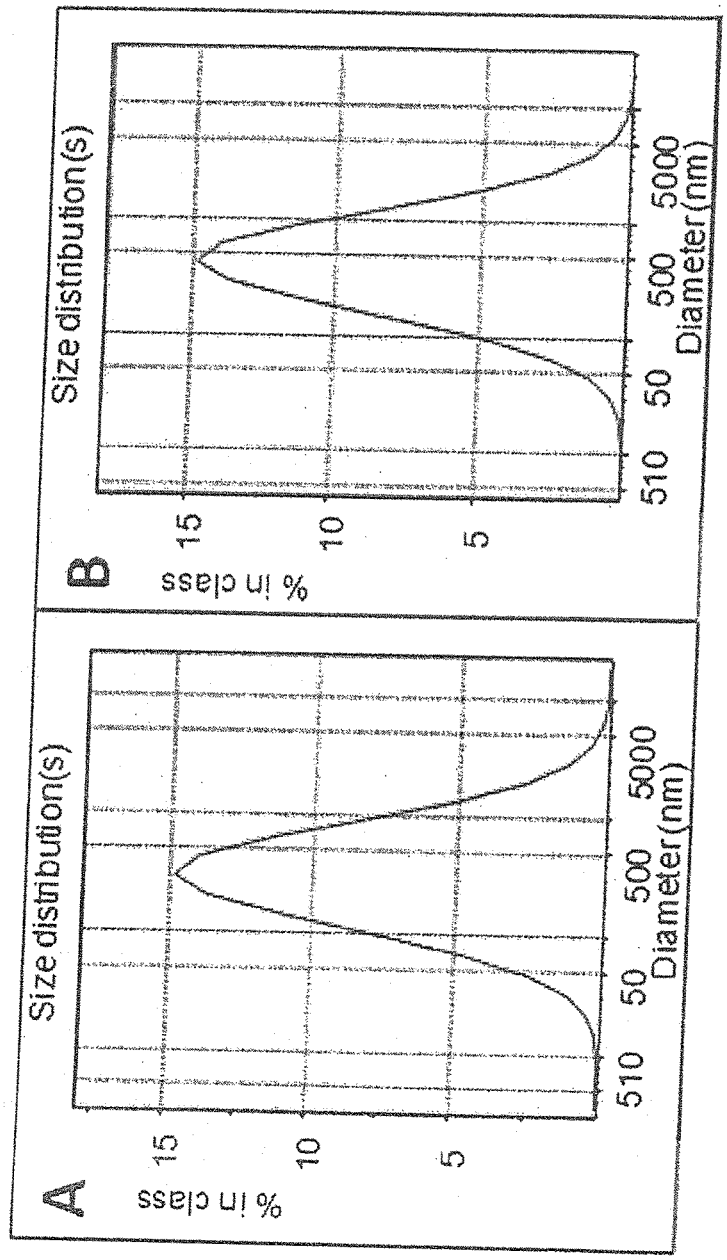
FIG. 5A shows Dynamic light scattering (DLS) analysis (A and B) and scanning electron microscopy (SEM) (C and D) of CS beads (A and C) and one embodiment of a biospecific contrast nanoparticle according to the invention (B and D).
Figure 5:
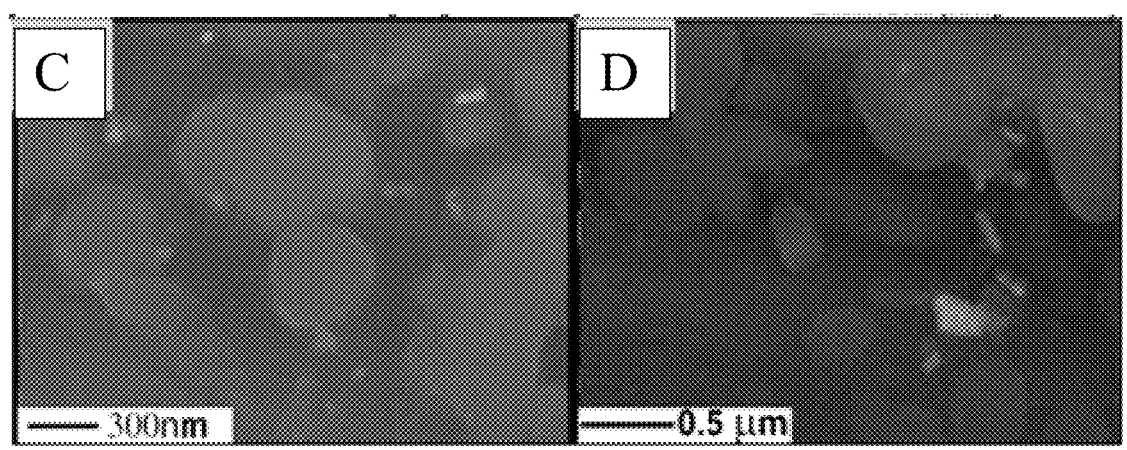
FIG. 5E is a schematic representation of one embodiment of a nanoparticle of the invention.
Figure 5E:
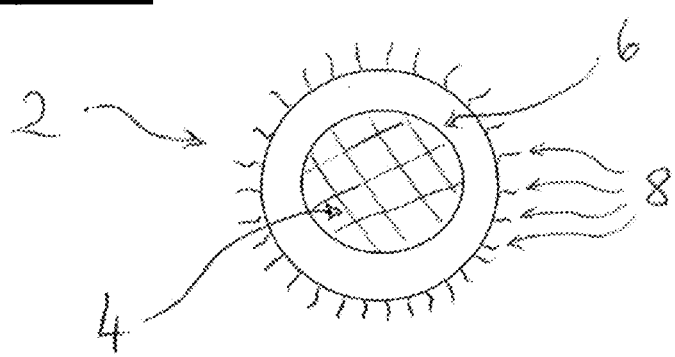

The inventors were interested in providing improved apparatus and methods for the diagnosis (e.g. by either MRI or CT imaging) or treatment of bone-related conditions. Accordingly, they have designed and developed novel bone specific agents 2 (e.g. nanoparticles, sub-micron particles, and atomic or molecular elements), as illustrated in FIG. 5E, which include a contrasting agent core 4 (e.g., an ion oxide or a gold metallic core), which is coated with a polymer 6 (for example, chitosan), which itself is derivatised or functionalised with one or more peptide(s) 8, which recognise bone cells (such as osteocytes, osteoblasts), or other peptides that are only present in bone, for example hydroxyapatite-specific peptides. Depending on the careful selection of the material in the core 4, of the polymer coating forming the outer shell 6, and of the bone-specific functionalising peptides 8 attached to the polymeric outer shell 6, the nanoparticles 2 etc. can be used in either diagnosis or therapy. For example, the particles 2 may be used in imaging bone remodelling activities, detecting pathological conditions and/or tissue repair processes. The following Examples describe the results of their research.

Example 1—Conjugation of Succinic Anhydride to Chitosan

The inventors have shown that chitosan (CS), a polysaccharide which can be used to coat contrast agents or other active ingredients of a pharmaceutical agent, can be conjugated to succinic anhydride. Chitosan succinate conjugates are known in the art as being both a biocompatible and biodegradable drug delivery agent which may be used in tablets.

1. Materials and Methods
(i) Chitosan (CS) Derivatisation
CS was derivatised by succinic anhydride (Suc-Chi) using a known ring opening reaction (Yan et al., 2006, Yakugaku Zasshi, 126, 789-793). A 1% (w/v) CS solution (in 1% v/v acetic acid) was filtered through 0.8 µm pore membrane (Millipore) and diluted (1:4) with methanol. Succinic anhydride (>99% GC, Sigma Aldrich) was dissolved in 5 ml acetone at 4% (w/v) was added drop wise under magnetic stirring and left overnight under agitation at room temperature. The gel that formed was removed from excess solution, double diluted in methanol and dialyzed against ultrapure water for 3 days.

The water was changed twice per day and the obtained precipitate was then collected by centrifugation and lyophilised.

(ii) Production of Suc-Chi Submicron Beads (i.e. Nanoparticles)

Suc-Chi beads were produced using an established ionic gelation method (Agnihotri, et al., 2004). Briefly, sodium tripolyphosphate (TPP) solution (1 mg/ml) was added drop wise to a 1 mg/ml Suc-CS solution (as described above) under magnetic stirring at a volume ratio of 1:5 and allowed to react for 45 minutes at room temperature. To produce magnetic resonance imaging (MRI) or CT imaging biospecific contrast agents (i.e. nanoparticles 2 of the invention), iron oxide core 4 particles ($Fe_3O_4$, 10 nm mean diameter) or gold core 4 particles (<20 nm mean diameter) were first dispersed in the TPP solution using ultrasonication before addition to Suc-CS solutions. The weight of the core particles 4 added was half that of the dissolved polymer 6. The core 4 particles were then washed by centrifugation through ethanol (to sterilise) and then in ultrapure water and reconstituted in sterile PBS.

(iii) Peptide Synthesis

The peptides 8 listed in Table 1 and their corresponding amino acid sequences were synthesised and then used to functionalise the core particles 4.

TABLE 1

List of typical peptides to be used for contrast agent biofunctionalisation

| Name | Sequence | Function |
|---|---|---|
| $GAP_{27p}$ | SRPTEKTIFII | Derived from $Cx_{43}$ $GAP_{27}$. To be used to block osteoclast-osteoclast and osteoclast-osteoblast (Chaytor, et al., 1997, Ilvesaro, et al., 2001) |
| $OP_{3-1}$ | YCLEIEFCY | Based on OPG residual 113-122. Specifically bind to RANK and inhibit RANKL induced osteoclast differentiation and activity (Cheng, et al., 2004, Shin, et al., 2008, Ta, et al., 2010) |
| $OP_{3-4}$ | YCEIEFCYLIR | Based on OPG residual 113-122. Specifically bind to RANK and inhibit RANKL induced osteoclast differentiation and activity (Cheng, et al., 2004, Shin, et al., 2008, Ta, et al., 2010) |
| $G_1PL$ | K-(KK) | Nanosized flexible carrier of the peptides with improved solubility in aqueous solution (Lloyd, et al., 2007, Meikle, et al., 2011) |
| $G_2PL$ | K-(KK)-(KKKK) | |
| $G_3PL$ | K-(KK)-(KKKK)-(KKKKKKKK) | |

TABLE 1-continued

List of typical peptides to be used for contrast agent biofunctionalisation

| Name | Sequence | Function |
|---|---|---|
| $G_2PL$-$OP_{3-1}$ | (KKKK)-(KK)-K-YCLEIEFCY | Pro-drug: novel $OP_{3-1}$ tethered $G_2PL$ |
| DOTA-$OP_{3-4}$ | DOTA-KGG-YCEIEFCYLIR | Novel DOTA tethered $OP_{3-4}$ peptide for the chelation of MRI visible $Gd^{3+}$ |
| DOTA-Gd-$OP_{3-4}$ | DOTA-KGG-YCEIEFCYLIR | Novel MRI detectable $OP_{3-4}$ derivative with a $Gd^{3+}$ chelate |
| DOTA-Gd-FHRRIKA | DOTA-Gd-FHRRIKA | Novel MRI detectable osteoblast migration derivative with a $Gd^{3+}$ chelate |

Figure 10:
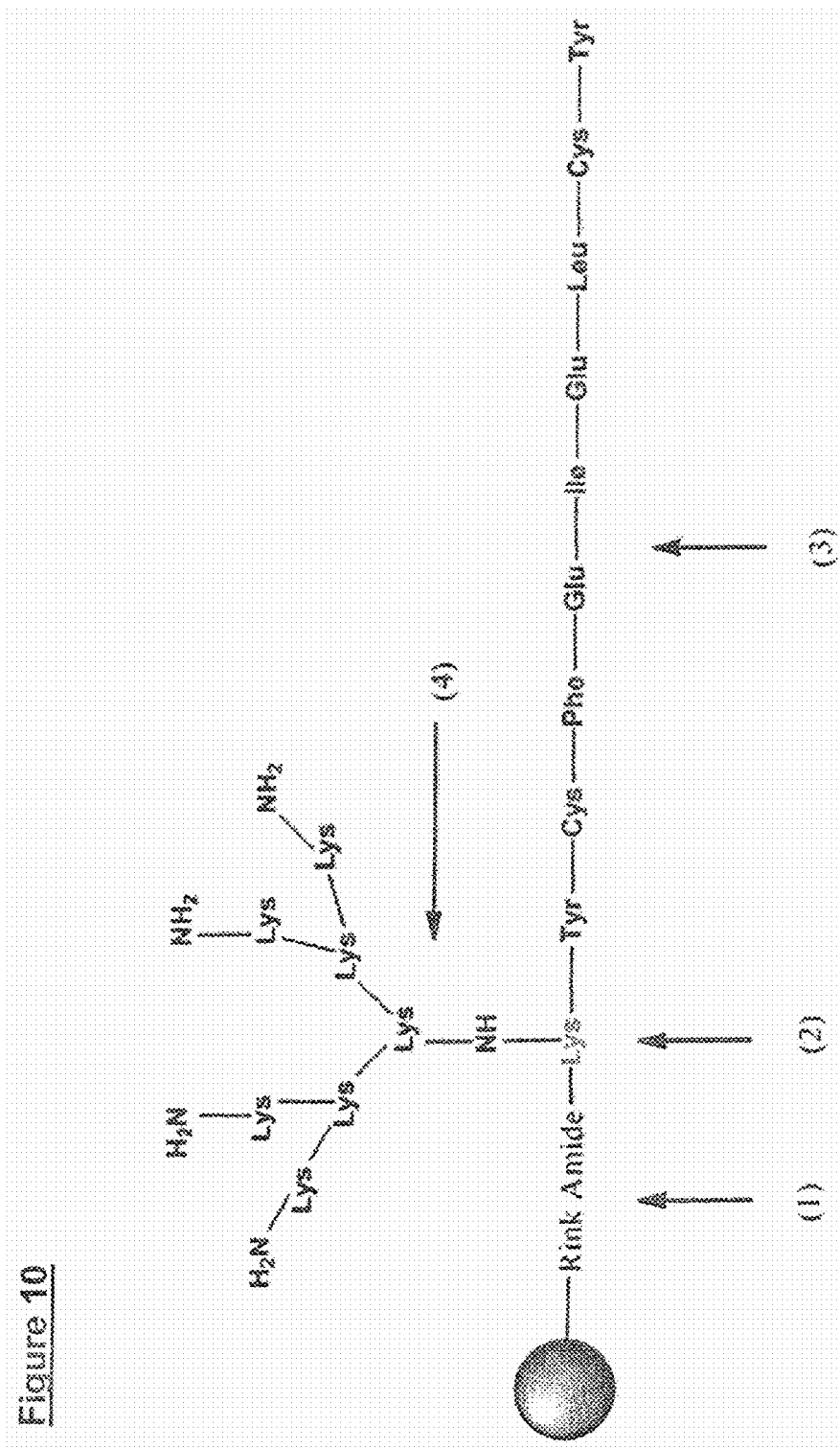
FIG. 10 is a schematic representation of the assembly of G2PL-OP3-1. Numbered arrows indicate the order of assembly.

NOTE:
$G_1PL$, $G_2PL$ and $G_3PL$ are not linear molecules, but rather hyperbranched (dendritic). See FIG. 10 where a $G_2PL$ molecule (vertical) is conjugated to $OP_{3-1}$ (horizontal).

The peptides 2 were synthesised by solid phase peptide synthesis (SPPS) using the conventional 9-fluorenylmethyloxy carbonyl (Fmoc) protection/deprotection strategy on Tenta Gel S $NH_2$ resin (0.1 mmol) and dimethylformamide (DMF) as the reaction solvent. An acid-liable Fmoc-Rink-Amide linker (linker) was attached first to the resin for later cleavage of the peptide 8. The peptide 8 was then synthesised by adding the first amino acid from the C-terminal followed by sequential coupling/deprotection steps of subsequent amino acids as per the peptide sequence, as set out in Table 1. The coupling reactions (30 minutes, x2) were carried out using HBTU (O-Benzotriazole-N,N,N',N'-tetramethyl-uronium-hexafluoro-phosphate), for amino group activation, and N,N-Diisopropylethylamine (DIPEA) as a tertiary base. The exposure of the protected amino groups was obtained by cleaving the Fmoc protecting group with 20% (v/v) piperidine in DMF (2 minutes, x3). In all preparations, the resin, linker and amino acids were added in the molar ratio of 1:4:4 respectively. HBTU and DIPEA (diisopropylethylamine) were 1 and 2 times the molar concentration of the amino acids respectively. Each coupling and/or deprotection step was followed by a washing step (x3 with DMF).

Osteoprogeterin (OPG) mimetic peptides, OP3-1 and OP3-4, as listed in Table 1, were cyclised by dimethyl sulfoxide (DMSO) oxidation to form cysteine-cysteine disulfide bonds as described in (Góngora-Benítez, et al., 2011). OP3 is a segment on OPG protein. RANKL on the surface of osteoblast (sometimes release in soluble form) interacts with RANK on osteoclasts, thereby initiating a reaction cascade leading to osteoclast differentiation and increased activity. OPG (released by osteoblasts) is a decoy for RANKL and its binding to RANK inhibits RANKL-RANK interaction, thereby stopping the cascade. Hence, OPG mimetics would act as ligands for the receptors in the bone-associated target cells. After synthesis, the peptides to be cyclised were cleaved from resin in a nitrogen atmosphere for 3 hours. After cleavage, the peptides were collected in cold diethyl ether, isolated by centrifugation and dried over a stream of nitrogen. The peptides were then dissolved in 600 ml of oxidising buffer (100 mM $NaH_2PO_4$ and 2 mM Gdn.HCl, 5% DMSO, pH 7.0) and shaken for 12 hours. The solution was then acidified with 1 M $HCO_2H$ (250 µl) and purified by LC-MS. The pure fractions were combined and freeze dried. The degree of cyclisation (formation of disulfide bridges) was assessed by the conventional method for quantitation of free thiol groups using Ellman's reagent. The peptides were ultimately characterised by HPLC and MS.

(iv) Production of Peptide-Tethered Biospecific Contrast Agents (i.e. Nanoparticles)

The peptides 2 described above were covalently attached to the core 4 particles by carbodiimide chemistry in order to create nanoparticles 2 of the invention. Non-derivatised particles were first dispersed in 2 ml of 2-(N-morpholino) ethanesulfonic acid (MES) buffer (0.1 M MES, 0.3 M NaCl, pH 6.5) to obtain a 1 mg/ml bead concentration. The carboxyl groups within the core 4 particles were then activated by addition of 1-ethyl-3-(3-dimethylaminopropyl) carbodiimide (EDC, 4 mM) and N-hydroxysuccinimide (NHS, 10 mM). The activation reaction was allowed to proceed at room temperature for 30 minutes. Excess EDC was deactivated by addition 13-mercaptoethanol (2.8 µl) and the core 4 particles were washed through a desalting membrane. A 1 mg/ml solution of the peptide chosen from Table 1 (e.g. OP3-4 peptide having the sequence, YCEIEFCYLIR) in MES buffer was then added to the solution of core 4 particles at a volume ratio of 1:1. The conjugation reaction was allowed to proceed under magnetic stirring for 3 hours at room temperature. The reaction was then quenched by the addition of hydroxylamine to give a final concentration of 5 to 10 mM.

Figure 1:
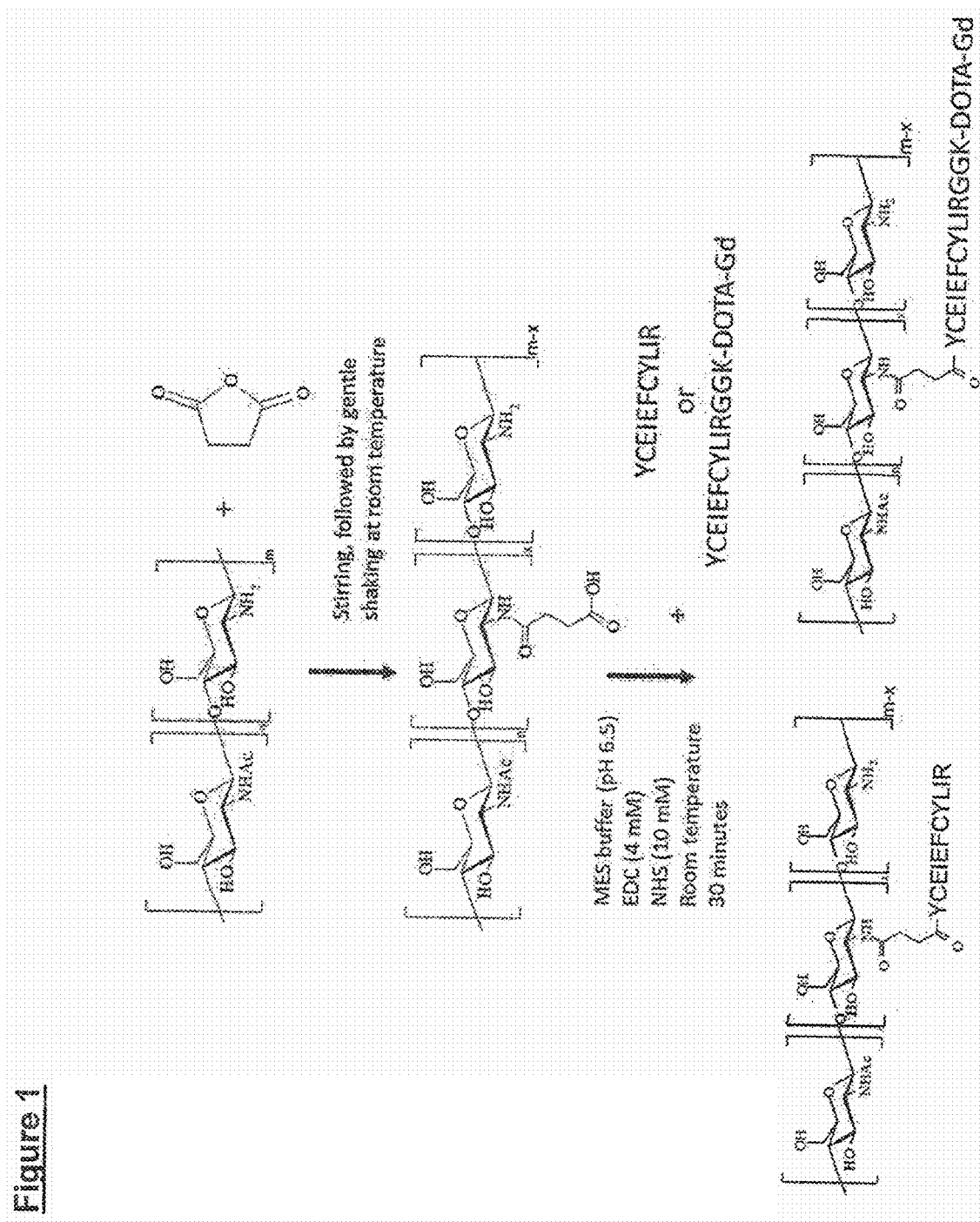
FIG. 1 shows a scheme of reaction of chitosan (CS) derivatisation by succinic anhydride to form succinate derivatised chitosan (Suc-Chi)

Referring to FIG. 5E, there is shown a schematic representation of one embodiment of the nanoparticle 2 of the invention. The Figure shows the nanoparticle 2 having the inner core 4 (e.g., ion oxide or gold) coated with the polymeric outer shell 6 (e.g. chitosan). The shell 6 is functionalised with a coating of peptides 8, which recognise bone cells, or other peptides that are only present in bone, for example hydroxyapatite. The resultant nanoparticles 2 were then purified using ultrafiltration spin columns (MWCO 100,000), lyophilised and stored at −20° C. FIG. 1 shows the scheme of the derivatisation of CS into Suc-Chi and its subsequent functionalisation with the OP3-4 peptide.

2. Results

Figure 2:
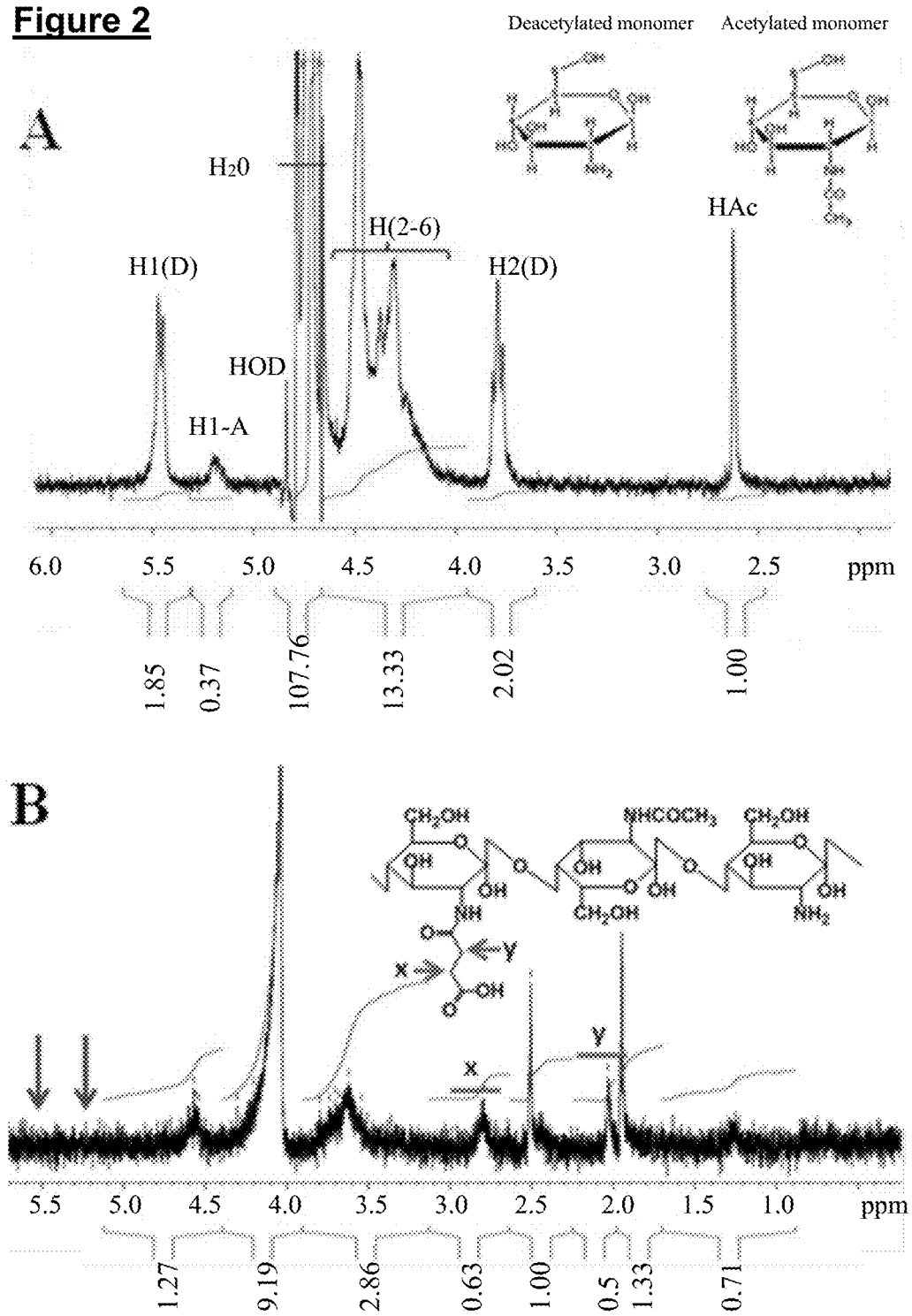
FIG. 2 shows NMR data of underivatised chitosan (CS, A) and derivatised chitosan (Suc-Chi, B). Vertical arrows in (B) show the disappearance of peaks present in the non-modified CS.

The $^1$H NMR spectra of CS and Suc-Chi are shown in FIG. 2. Briefly, the signals are assigned as follows: 2.50-2.70 ppm (H—Ac) was attributed acetyl proteins of GlcNAc monomers; 2.50-2.75 ppm (H2D) was attributed to proton 2 of GlcN monomer; 3.95-4.65 ppm (H2-2) was attributed protons 2 to 6 of both GlcNAc and GlcN monomers; 4.65-4.90 ppm (HOD) corresponds to the solvent (HOD); 5.10-5.30 ppm (H1-A) corresponds to proton 1 of GlcNAc monomers; 5.30-5.65 ppm (H1-D) correspond to proton 1 of GlcN monomer. When compared to the spectra of CS, the spectrum of Suc-Chi confirms successful attachment of succinic anhydride to CS. This is seen in the poorly resolved or missing signal for H1(D), H1-A and H2D within the range 5.00-5.70 ppm (see FIG. 2B, arrows, for the first two) and 3.6-3.9 ppm for H2D. The new signals in the range 2.34-2.57 ppm, seen in the spectra of Suc-Chi but absent in the spectra of CS, are attributed to the two methane hydrogen groups (—COCH$_2$CH$_2$COOH) of the succinyl group and is in agreement with reports by others (Liang, et al., 2012, Xiangyang, et al., 2007).

Figure 3:
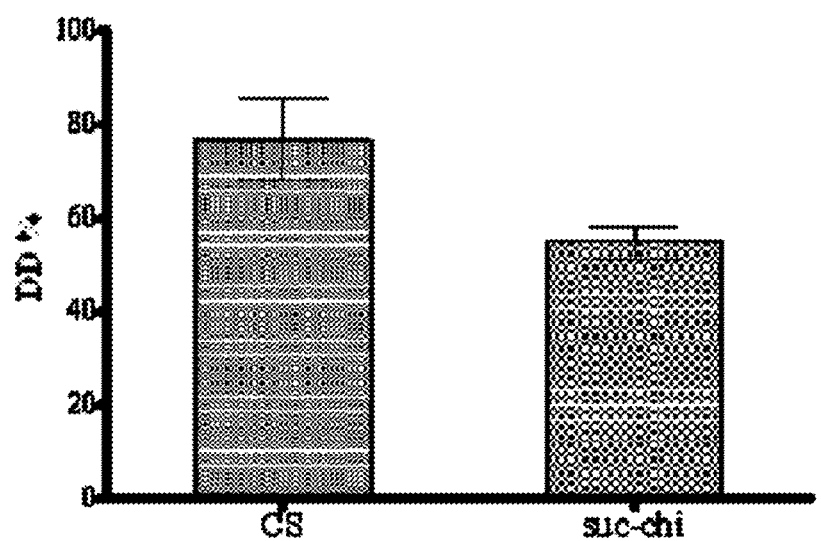
FIG. 3 shows the degree of derivatisation of CS with succinic anhydride in suc-chi compared to underivitised CS.

The degree of substitution as determined by titration was 25.5% and 30.6% by $^1$HNMR. Although, less accurate, potentiometric titration analysis allowed for the determination of the molar amounts of the free —NH$_2$ in both CS and Suc-Chi. The degree of derivatisation (DD) values calculated for CS was 79.92% (+5.85) and for Suc-Chi was 54.4% (±3.7), as shown in FIG. 3. The titrations were repeated 5 times for both polymers. These data suggest a reduction in the amount —NH$_2$ groups after derivatisation of CS with succinic anhydride. The presence of non-derivatised —NH$_2$ groups was important to ensure the CS cross-linking by TPP during nanoparticle 2 production.

Figure 4:
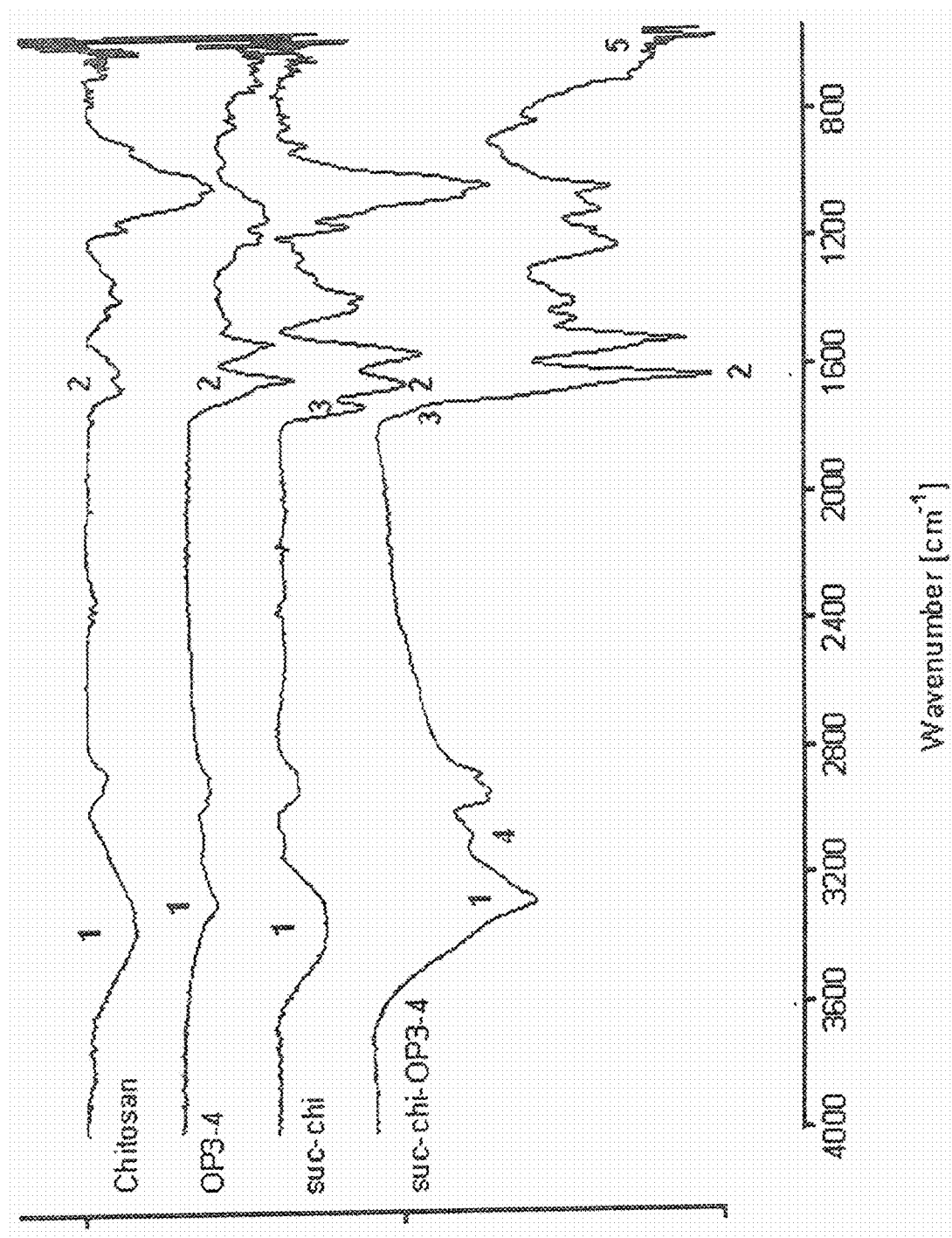
FIG. 4 shows an FTIR spectra of CS derivatisation into Suc-Chi and its functionalization with an OP3-4 peptide which has the following amino acid sequence YCEIEFCYLIR.

FTIR results also showed successful derivatisation of chitosan to Suc-Chi and subsequent attachment of OP3-4, as shown in FIG. 4. N—H stretch of primary and secondary amines and O—H stretch are comprised in band 1 (3500-3200 cm$^{-1}$). The main contribution to band 1 in the spectra of OP3-4 is from the amines involved in the amide bond. Band 2 (1640-1580 cm$^{-1}$) may correspond to the N—H deformation in primary amines, present in the four species; N—H deformation of amides and also carbonyl stretching in secondary amides for the case of OP3-4, Suc-Chi and Suc-Chi-OP3-4. Band 3, (1722 cm$^{-1}$), which is present in Suc-Chi and unresolved in Suc-Chi-OP3-4 may be attributed to the carbonyl stretching as result of the linkage of the succinyl group to the polysaccharide through an ester bond, in addition to the linkage via amide bond described earlier (band 3). The aromatic structures present in tyrosine and phenylalanine can be confirmed in Suc-Chi-OP3-4 with band 4 (3000 cm$^{-1}$), which originates from C—H stretch in unsaturated species. A large peak at band 5 (500-540 cm$^{-1}$) in the spectrum of Suc-Chi-OP3-1, which is weakly present in the OP3-4 sample and absent in Suc-Chi and CS can be attributed to the presence of disulfide bonds.

From the results obtained by $^1$HNMR and titration, it was concluded that succinyl groups were successfully conjugated to the amine groups in CS. FTIR results further suggest the successful attachment of the OP3-4 peptide to Suc-Chi.

Figure 6:
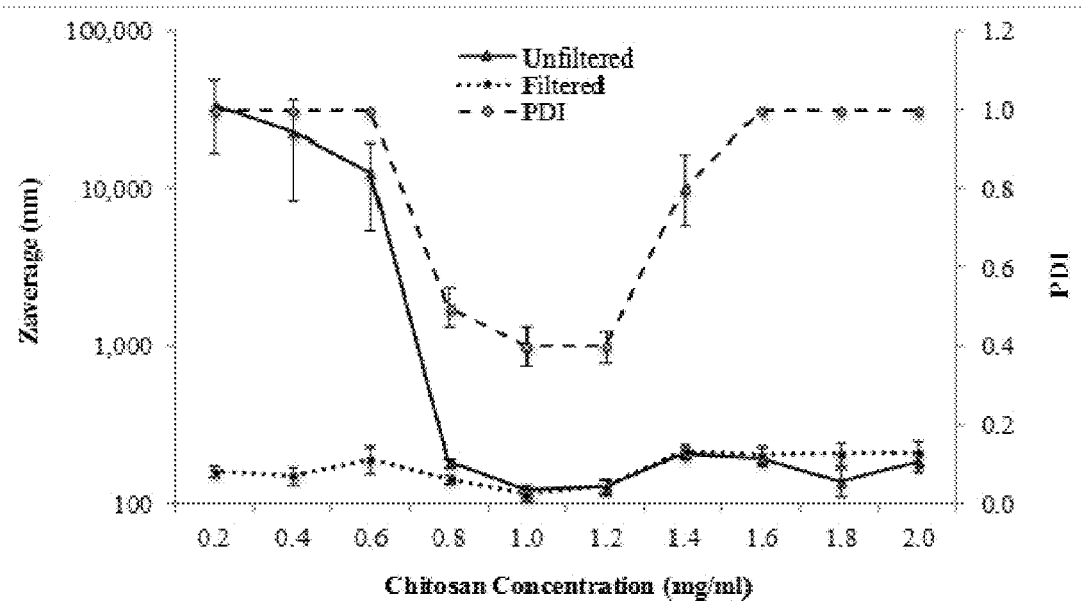
FIG. 6 shows the effect of chitosan concentration on nanoparticle size without and with filtration process. (A) 150 molecular weight, (B) 400 molecular weight, (C) 600 molecular weight, (D) Concentration-dependence in different molecular weight Ch (n=4)
Figure 6:
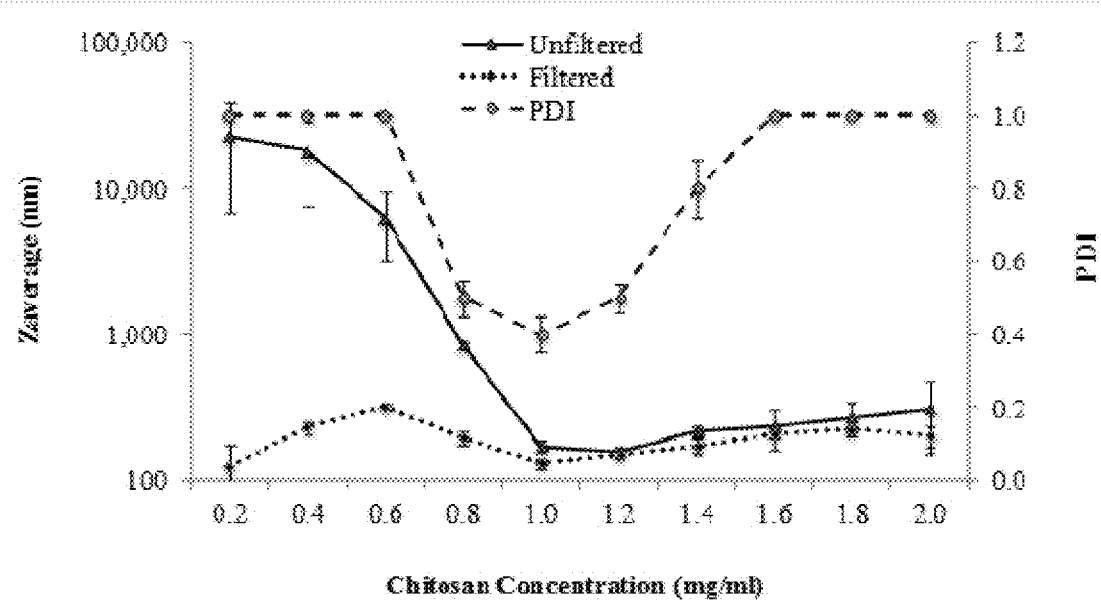
Figure 6:
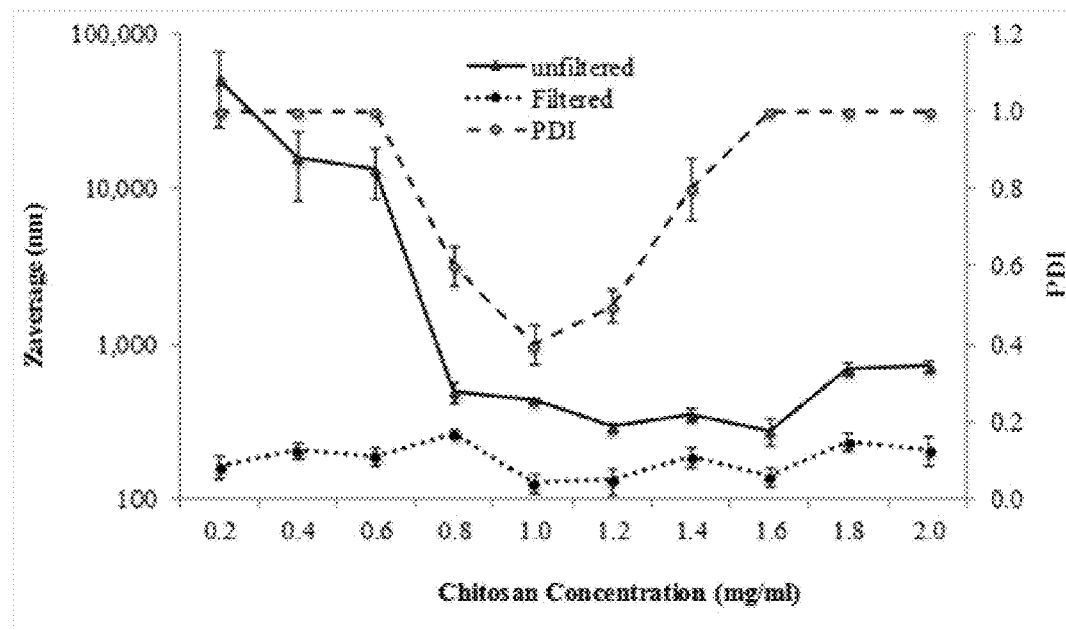
Figure 6:
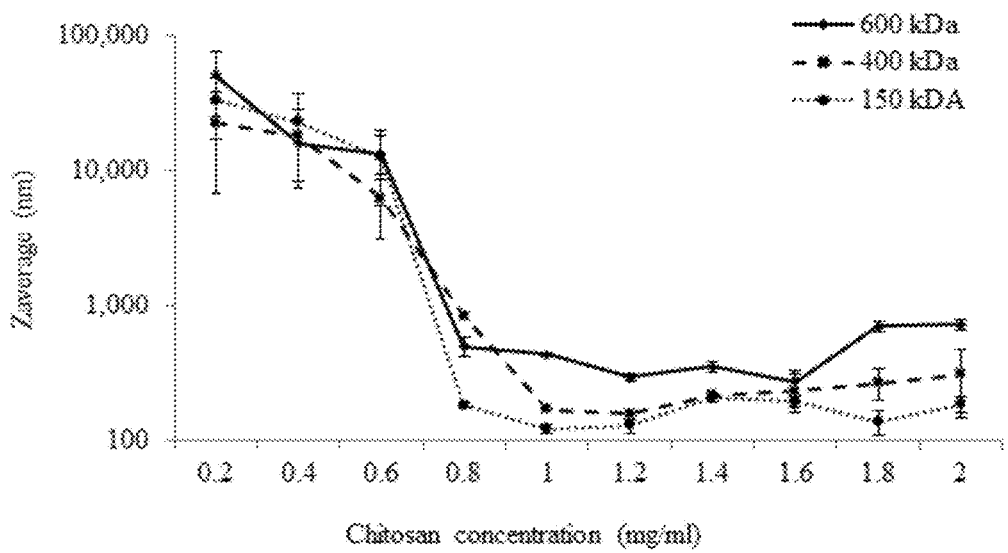

Dynamic light scattering analysis (DLS) and scanning electron microscopy (SEM) showed that the nanoparticles had an average hydrodynamic diameter ($Z_{average}$) of 366.4 nm (polydispersity index, PDI of 0.4), which increased to 408.3 nm (PDI of 0.5) after incorporation of Fe$_3$O$_4$ core 4 particles (10 nm) to produce MRI detectable nanoparticles 2, see FIGS. 5A-D. Changes in chitosan molecular weight, and concentration without or with the filtration step allowed the tuning of the nanoparticle 2 size and polydispersity index (PDI), see FIGS. 6 A-D.

Example 2—Conjugation of OP3 with DOTA

The inventors then set out to determine whether the protein, osteoprogeterin 3 (OP3), which is specifically expressed on bone cells, such as osteoclasts and oseoblasts, can be conjugated to Dotarem (DOTA), which is a chelator that can be used to coat various contrast agents, including gadolinium. Dotarem is gadoteric acid, a known macrocycle-structured GD-based MRI contrast agent. It consists of the organic acid DOTA as a chelating agent.

1. Materials and Methods

Figure 7:
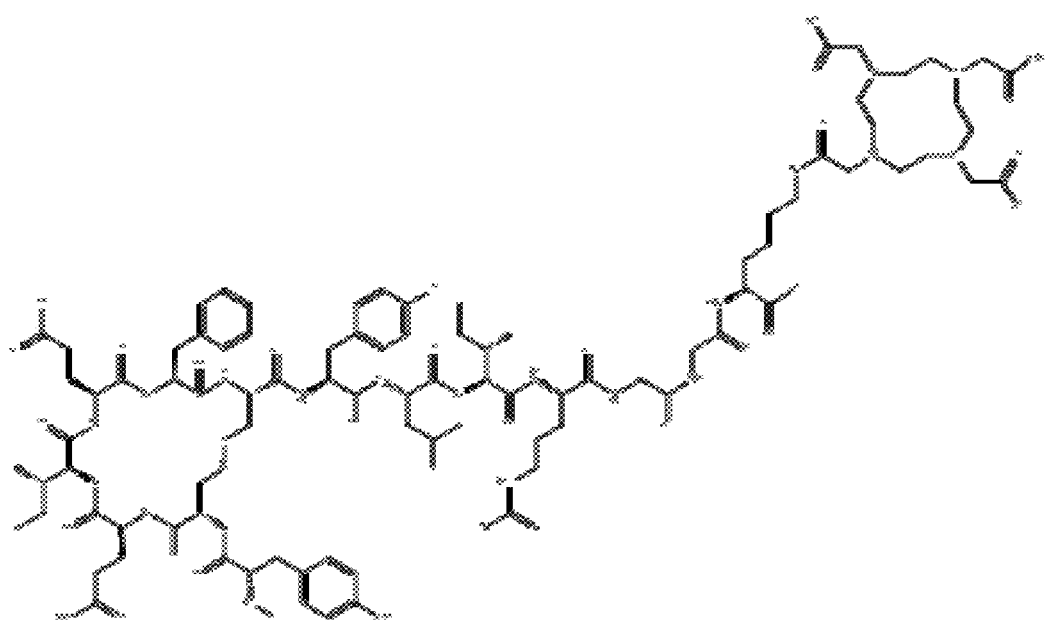
FIG. 7 shows the typical structure of a DOTA-OP3-4, i.e. the result of the conjugation of the OPG mimetic peptide, (OP3-4), which specifically targets cytokines expressed on bone cells, to DOTA, which can be used to chelate several metal ions such as gadolinium ($Gd^{3+}$) as contrast agents.

A novel DOTA-OP3-4 conjugate protein was synthesised by solid phase peptide synthesis using Fmoc chemistry as described in the synthesis of OP3-1 and OP3-4. In this case, however, lysine core amino acid was added first, followed by the coupling of DOTA to the NH$_2$ group that was protected by Mtt. Two glycine amino acids were then coupled to form a spacer followed by the subsequent assembly of OP3-4 peptide. The introduction of the lysine-glycine-glycine spacer between DOTA molecule and OP3-4 sequence was considered important to avoiding potential steric hindrance during the synthesis and any possible effect on the potency of the peptide. A structure of the DOTA-OP3-4 is shown in FIG. 7.

Figure 8:
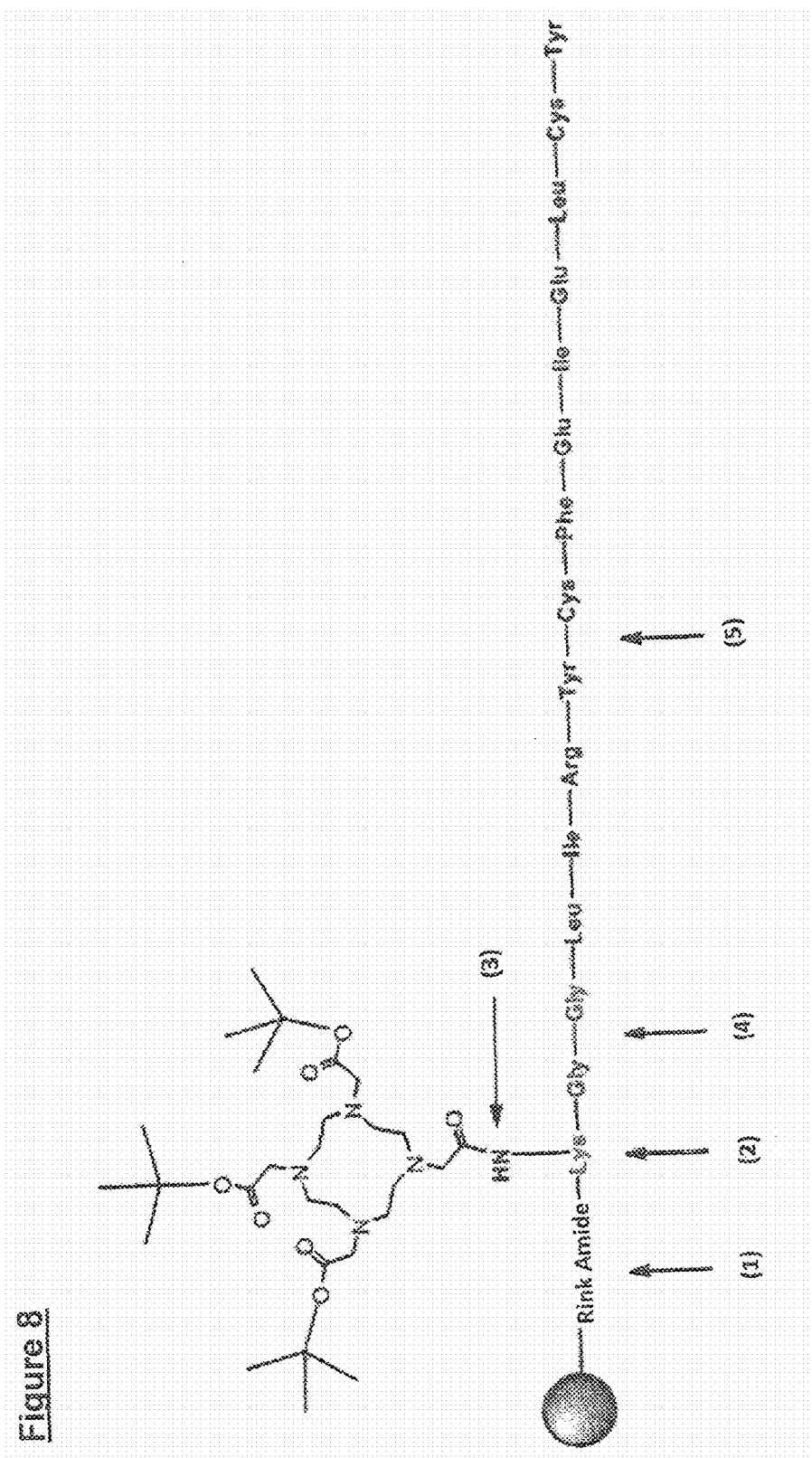
FIG. 8 is a schematic representation of the assembly of DOTA-OP3-4. Numbered arrows indicate the order of assembly.

The same solid phase peptide synthesis method was used to synthesise novel derivatised biospecific peptides with linear (see FIG. 8) or branched (see FIG. 10) ends able to favour the stable binding of the peptides to the contrast agents.

2. Results

Figure 9:
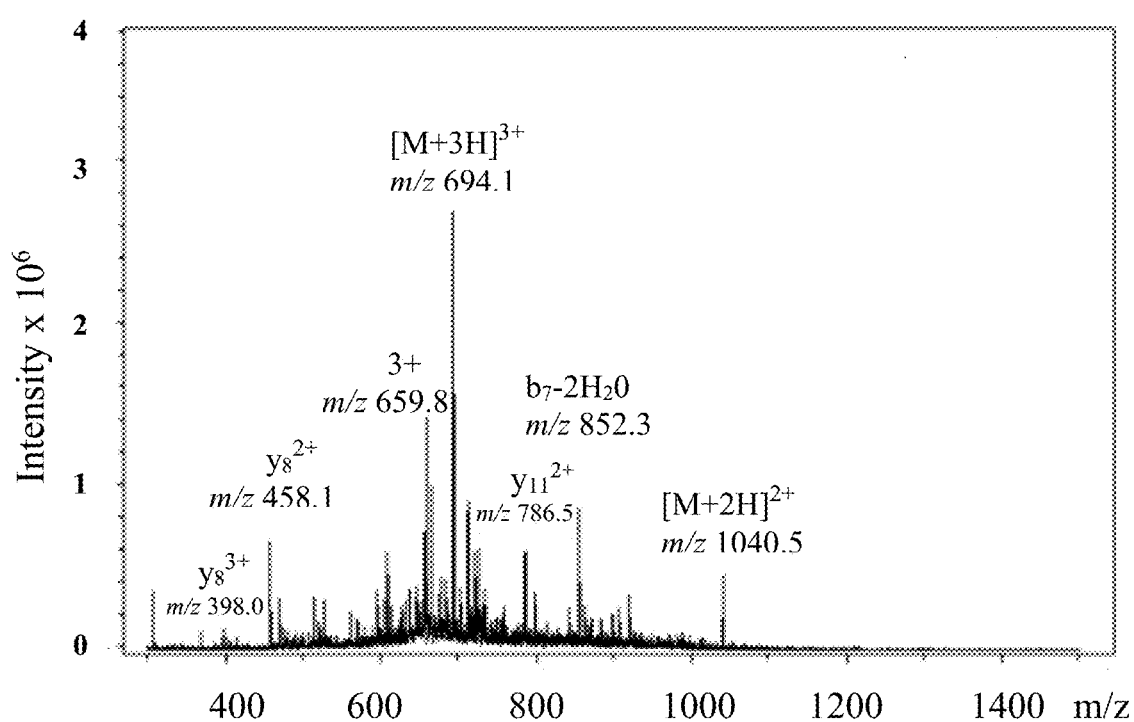
FIG. 9 shows an ion trap MS spectrum of DOTA-OP3-4.
Figure 11:
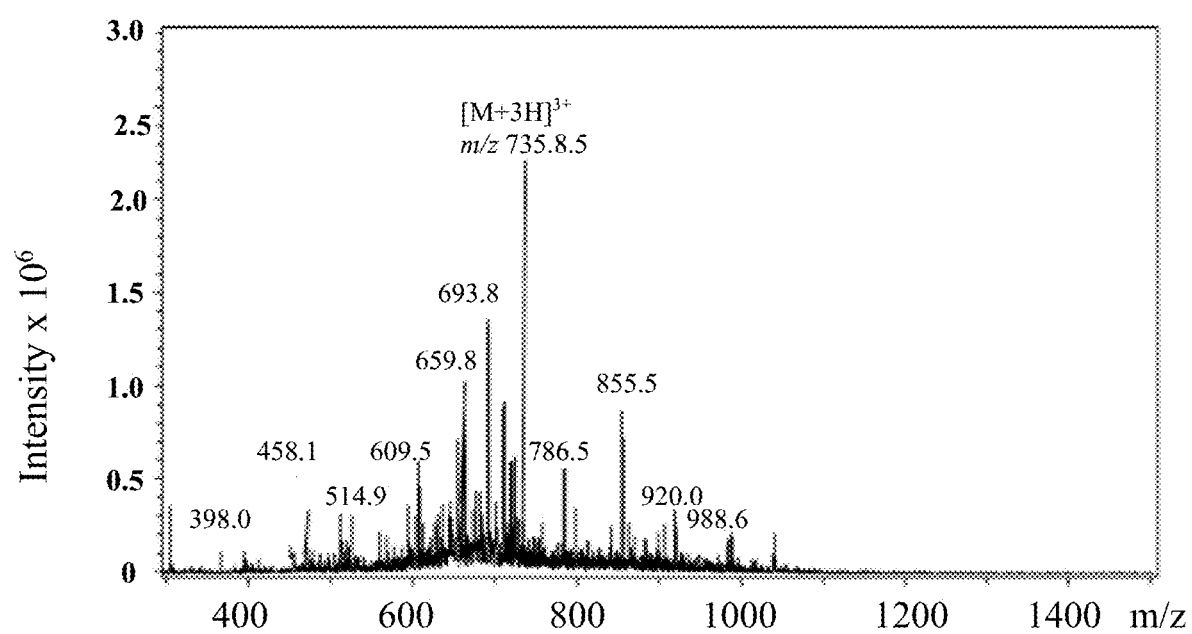
FIG. 11 shows an ion trap MS spectrum of G2PL-OP3-1.

FIGS. 9 and 11 show typical mass spectrometry spectra of a linear (FIG. 9) and a branched (FIG. 11) OP3-4 peptide. These prove the successful synthesis of these peptides that is necessary to the formation of stable binding and functionalisation to the core 4 particle. Purity of above 95% was achieved after purification procedure.

Example 3—Creation of a Biospecific Contrast Agent—DOTA-Coated Gadolinium, which is Conjugated to OP The inventors next set out to determine whether a gadolinium (Gd)-based contrast agent could be created to form a nanoparticle 2 of the invention by the conjugation of DOTA-coated Gd with the bone-specific protein osteoprogeterin 3 (OP3). The hope was that they could also be used with MRI and/or CT imaging techniques.

1. Materials and Methods

Novel peptides were used to manufacture biospecific contrast agents (i.e. functionalised nanoparticles 2) for MRI and CT (see Table 1). The chelation of the core 4 particle, $Gd^{3+}$, was achieved by incubating DOTA-OP3-4 with $GdCl_3$ in a buffer system for 15 hours. The DOTA moiety acted as a polydentate ligand and enveloped the metal cations, in this case complexing $Gd^{3+}$, to give an MRI-visible peptide. The coordination of the DOTA ligands and metal ion in the complex depends on the conformation of the ligand and geometric tendencies of the metal cation. On its own, DOTA acts as an octadentate ligand, binding the metal through four amino and four carboxylate groups. In this study, the DOTA molecule acts as a septadentate since one of the carboxylate groups is used in the covalent with the peptide. However, a carboxylate group from the amino acid linking DOTA and the peptide provides the eighth ligand and restores the octadentate state, forming a highly stable coordination complex (Viola-Villegas, et al., 2009).

The resultant nanoparticles 2 were obtained through the direct binding of peptides 8 with a linear or branched root to magnetic core 4 particles (e.g. iron oxide) coated with thin films of polymers 6 or ceramics (i.e. MRI contrast agents) or gold core 4 particles (i.e. CT contrast agents). In this case, surface functionalization of polymeric carboxylic groups or hydroxyl groups of polymers 6 and ceramics were activated and derivatised with an amino acid to which a selected biospecific peptide from Table 1 was grafted through covalent binding.

2. Results

Figure 12:
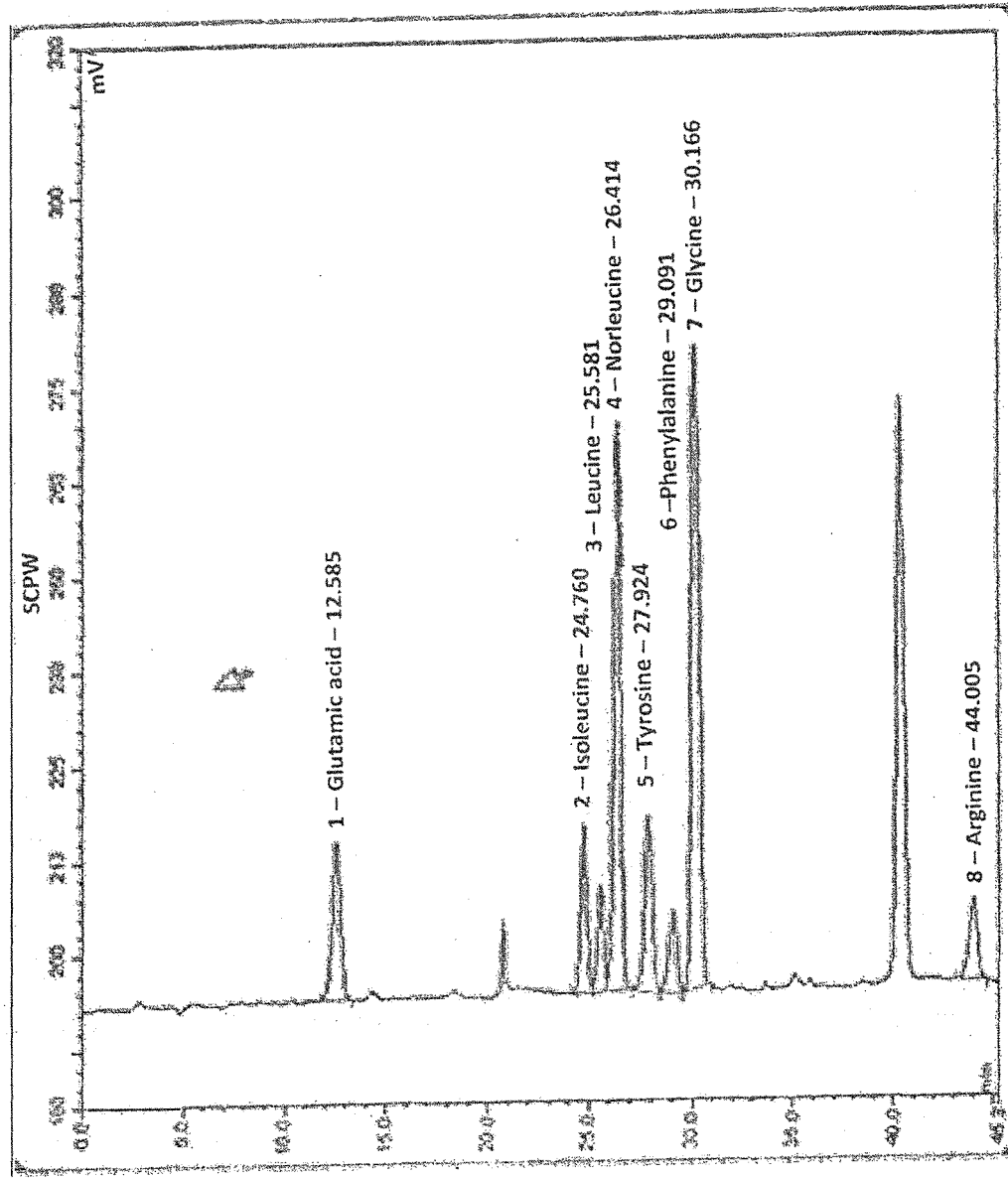
FIG. 12 shows amino acid analysis of OP3-4 peptide on a nanoparticle and on a nanoparticle-DOTA-Gd-OP3-4 conjugate.

Successful chelation of $Gd^{3+}$ was confirmed by LC-MS where the peak with m/z 694.1 for DOTA-OP3-4 peptide was replaced by a peak with m/z 714.8 corresponding to the $[M+3H]^{3+}$ after chelation of $Gd^{3+}$. Amino acid analysis confirmed the successful attachment of OP3-4 to the gadolinium (Gd)-based nanoparticle 2 (FIG. 12). After hydrolysis, the amount of glucosamine units and the amount of amino acids present in the polymer was determined. The amount of peptide 8 attached onto the nanoparticle 2 was calculated by the integration of peak areas. A representative LC profile of the hydrolysis products on the Gd nanoparticle 2 functionalised with the OP3-4 peptide 8 is given in FIG. 12. The glucosamine units per micro gram of material was calculated to be 1.92 nmoles in chitosan-based nanoparticles (CNB), 1.40 nmoles in Gd core 4 particle (on its own) and 0.27 nmoles in Gd nanoparticle 2 functionalised with OP3-4 peptide 8, and Gd nanoparticle-DOTA-Gd-OP3-4.

Importantly, in both nanoparticle-OP3-4 and nanoparticle-DOTA-Gd-OP3-4, the amount of peptide 8 conjugated was calculated to be 4.2 mmoles per gram of nanoparticle 2. Individual amino acids were detected in molar ratios reflective of the amounts in OP3-4 sequence.

Example 4—Testing the Use of the Nanoparticles with MRI

The inventors then tested their biospecific peptide-functionalised nanoparticles 2 for positive MRI signalling under T1 and T2 modes. Biospecific nanoparticles 2 were obtained through the entrapment of Gd core 4 into derivatised peptides 8 and by grafting onto nanoparticles previously functionalised with bioactive peptides.

1. Materials and Methods

The solutions of the peptides (DOTA-OP3-4 and DOTA-Gd-OP3-4) in PBS buffer were prepared by first dissolving the peptides in a minimum amount of DMSO and then diluted out to give a 20 µg/ml peptide stock solution in PBS (1% DMSO) and the pH adjusted to 7.2 with 0.1M HCl. The various nanoparticles 2 (i.e. core 4 particle alone, nanoparticle-OP3-4 conjugate, nanoparticle-DOTA-Gd-OP3-4 conjugate) were suspended in the same PBS buffer solution. Stock solutions DOTA-$Gd^{3+}$ (20 µg/ml) and $Fe_3O_4$ nanoparticles (10 nm, 20 µg/ml) were prepared and used as a positive controls for gadolinium based and $Fe_3O_4$ based contrast agents respectively.

A comparison of the nanoparticle-OP3-4 conjugate and nanoparticle-DOTA-Gd-OP3-4 conjugate was carried out first. For this, Whatman filter papers (circular, 15 mm diameter, cat: 1441 150, USA) were soaked in the stock solutions.

In the studies on the effect of the concentration of the nanoparticles 2 and peptides 8, different concentrations of the peptides 8 and nanoparticles 2 were prepared by a series of double dilutions of the stock solutions. The concentrations of DOTA-Gd-OP3-4 was (10, 5, 2.5, 1.25, 0.625, 0.313, 0.078, 0.039, 0.020, 0.010, and 0.005 µg/ml) and for core 4 particle alone was (20, 10, 5, 2.5, 1.25, 0.625, 0.313, 0.078, 0.039, 0.020 and 0.010 µg/ml). The analytes were then placed in 24 well culture plates at a volume of 500 µl per well. All MRI imaging was performed on using a Siemens AVANTO 1.5T MRI scanner at the Clinical Imaging Science Centre, Brighton and Sussex Medical School, UK.

2. Results

FIG. 13 shows a typical MRI scan of a negative control filter impregnated with phosphate buffered saline (PBS), a negative control consisting of DOTA-OP3-4 peptide 8 but with no contrast agent core 4, and a gadolinium-chelating DOTA-OP3-4 nanoparticle 2. The scan clearly show that while the negative control showed only noise signals, the peptide 8 chelating the gadolinium core 4 provided a clear positive signal. A comparative analysis of filters impregnated with either gadolinium-chelating DOTA-OP3-4 and peptide-functionalised magnetic nanoparticle 2 showed the typical bright and dark images expected from the two contrast agents in the chosen mode of detection (FIG. 14).

Example 5—Testing the Inhibitory Effect of OP and OP4-Conjugated Nanoparticles in Vitro The inventor next determined whether a nanoparticle 2 comprising DOTA-coated gadolinium core 4 conjugated to osteoprogeterin 3 or 4 (OP3 or OP4) peptide 8, would inhibit osteoclastogenesis and osteoclast activity in vitro.

1. Materials and Methods

Osteoclasts were obtained from mononuclear cells freshly isolated from peripheral blood from healthy human donors according to conventional methods based either on spiking of the cells with RANK and M-CSF or in osteoblast mononuclear cell co-culture systems spiked with M-CSF. Peptides and peptide-tethered nanoparticles 2 (i.e. nanoparticle-OP3-4, magnetic nanoparticle-OP3-4, nanoparticle-OP3-DOTA and nanoparticle-OP3-4-Gd-DOTA) were added to the cells at peptide concentration equivalent of 50 µM as determined by amino acid analysis. The negative controls received no test materials and the positive control received rh OPG (50 ng/ml). Spiking was performed either before or after the differentiation of the mononuclear cells into osteoclasts.

Inhibition of osteoclastogenesis and osteoclast activity was quantitatively assessed by counting the number of TRAP positive multinucleated (MNC) cells using light microscopy and the number of MNC cells presenting F-actin rings using epi-fluorescence microscopy. Osteoclast activity was also assessed qualitatively by analysis of the number of resorption pits formed on the bone slices by SEM. Culture medium was replaced every 3 days with fresh medium supplemented with all the growth factors and test materials.

Three different approaches were used to determine inhibition of osteoclastogenesis and osteoclast activity. These methods were: (1) counting the number of TRAP positive multinucleated cells; (2) counting the number of multinucleated cells possessing the actin rings (MNC-AR+) using Hoechst 33258 and rhodamine phalloidin double stain; and; (3) determining the degree of bone resorption by assessment of resorption pits formed after culturing cells on bone slices. Where cells were too numerous to count microscopically, an image editing software (Image J v1.44P) was used to distinguish and count the cells. The software allows for cells to be tallied according to colour and shape for both osteoclast and non-osteoclast cells and the degree of osteoclastogenesis expressed was a percentage of TRAP positive cells per field (Labno).

2. Results

The result from the studies on the effect of nanoparticles 2 functionalised with OP3-4 and $Gd^{3+}$ chelating derivatives thereof on osteoclastogenesis are shown in FIG. 15. In all formulations, the modified peptides 8 free and bound to nanoparticles 2 and gadolinium reduced the formation of osteoclasts at levels significantly different from the control, but with different degrees of efficacy (FIG. 15).

In addition, peptide-functionalised magnetic nanoparticles 2 appeared to significantly reduce osteoclastogenesis when compared to non-functionalised nanoparticles (see FIG. 16). The number of TRAP positive MNC in culture treated with nanoparticle-OP3-4, nanoparticle-DOTA-OP3-4 and nanoparticle-DOTA-Gd-OP3-4 was not significantly different showing that the various modifications of the peptide and its grafting to nanoparticles 2 did not alter its ability to inhibit osteoclastogenesis. When used on its own, $Gd^{3+}$ is toxic both in vitro and in vivo. However, macrocydic chelates such as DOTA tightly trap $Gd^{3+}$ improve the ion solubility thus avoiding cytotoxic effects. Indeed Suc-Chi with its many free carboxyl groups and improved solubility would further contain $Gd^{3+}$ and improve the biocompatibility of DOTA-Gd-OP3-4.

A clear inhibitory effect on the activity of already differentiated osteoclasts is shown in FIG. 17.

Finally, the inhibition of the activity of differentiated osteoclasts was clearly observed by SEM showing the absence of pits produced by the control cells, as shown in FIG. 18.

SUMMARY

The diagnosis and treatment of bone pathologies (e.g. osteoporosis) with localised injection of agents is widely advocated. The inventors have now developed novel contrast agents for use in MRI and CT imaging, which agents can recognise bone cells, osteoblasts and osteoclasts, as well as the mineralized bone extracellular matrix. These biorecognition properties were obtained through the synthesis of novel derivatised peptides with specificity for various bone cells and the mineral phase of bone. The derivatisation was designed to favour the stable binding with contrast agents of nanoparticulate or ionic composition without affecting their imaging properties. Specific types of contrast agents in the form of magnetised polymeric beads, mainly chitosan nanobeads, were obtained either through methods of coating of the magnetic core or grafting of gadolinium-modified peptides or a dispersion of ions in their cross-linked matrix. This ability to recognise cellular and structural components of the bone was coupled with the ability of controlling the cell behaviour. Biospecific contrast agents able to recognise mononuclear cells during their process of differentiation into osteoclasts as well as to recognise and inhibit the activity of differentiated osteoclasts could be obtained together with agents able to favour osteoblast migration.

In summary:—
1. Surface functionalization of submicron particles, such as $Fe_3O_4$ nanoparticles (i.e. a MRI contrast agent) and gold nanoparticles (i.e. a CT contrast agent) with osteoblast- and osteoclast-specific peptides as well as with hydroxyapatite-specific peptides are preferred.
2. Gadolinium (i.e. a MRI contrast agent) and iodine or boro-sulphate (i.e. CT contrast agent) entrapped into polymeric beads functionalised with osteoblast- and osteoclast-specific peptides as well as with hydroxyapatite-specific peptides.
3. Gadolinium (i.e. MRI contrast agent) and iodine (i.e. CT contrast agent) complex with osteoblast- and osteoclast-specific peptides as well as with hydroxyapatite-specific peptides.
4. Nanoparticles formed by a coating of synthetic or natural polymers where the morphology and size is determined by the tuned physico-chemical properties of the polymer and where the biorecognition and bioactivity are obtained through its derivatisation with specific peptides capable of recognised tissue cells.
5. Nanoparticles formed by crosslinking (mainly ionically crosslinking) of synthetic and natural polymers (e.g. chitosan) previously derivatised with tissue-specific peptides, where crosslinking and biofunctionalisation are tuned to optimise the stability of the nanoparticle and the presentation of the biospecific/bioactive molecules. These nanoparticles include in their formulation dispersed contrast agents for MRI and CT.

In all cases, these biospecific agents couple the property of contrast agents with combined, built-in biorecognition and bioactivity properties capable of inducing tissue imaging and regeneration.

In vitro mono- and co-culture studies of osteoblasts and osteoclasts demonstrated the ability of bone-specific peptides to the cells. Given the ability of the osteoblast-specific peptides (e.g. FHRRIKA) to encourage cell processes and of the OPG-mimicking peptides to inhibit osteoclastogenesis, these novel material can be also used as theranostic (i.e. combined therapy and diagnostic) agents in the treatment of bone deficiencies.

REFERENCES

Agnihotri S, A, Mallikarjuna N, N & Aminabhavi T, M (2004). Recent advances on chitosan-based micro- and nanoparticles in drug delivery. Journal of Controlled Release, 100, 5-28.

Chaytor A T, Evans W H & Griffith T M (1997). Peptides homologous to extracellular loop motifs of connexin 43 reversibly abolish rhythmic contractile activity in rabbit arteries. The Journal of Physiology, 503, 99-110.

Cheng X, Kinosaki M, Takami M, Choi Y, Zhang H & Murali R (2004). Disabling of Receptor Activator of Nuclear Factor-KappaB (RANK) Receptor Complex by Novel Osteoprotegerin-like Peptidomimetics Restores Bone Loss in Vivo. Journal of Biological Chemistry, 279, 8269-8277.

Góngora-Benftez M, Tulla-Puche J, Paradis-Bas M, Werbitzky O, Giraud M & Albericio F (2011). Optimized Fmoc solid-phase synthesis of the cysteine-rich peptide linaclotide. Peptide Science, 96, 69-80.

Ilvesaro J, Tavi P & Tuukkanen J (2001). Connexin-mimetic peptide Gap 27 decreases osteoclastic activity. BMC Musculoskeletal Disorders, 2.

Labno C. (2011). Integrated Light Microscopy Core: Two Ways to Count Cells with ImageJ [Online]. University of Chicago. Available: http://digital.bsd.uchicago. edu/resources files/cell%20counting%20 automated%20and%20manual.pdf [Accessed Jan. 12, 2011 2011].

Liang N, Sun S, Li X, Piao H, Piao H, Cui F & Fang L (2012). α-Tocopherol succinate-modified chitosan as a micellar delivery system for paclitaxel: Preparation, characterization and in vitro/in vivo evaluations. International Journal of Pharmaceutics, 423, 480-488.

Lloyd A, William, John G, William, Heath H, Standen G, Matteo S & Meikle S, Thomas. 2007. Biomaterials with Functionalised Surfaces. U.S. patent application Ser. No. 12/517,705.

Meikle S T, Perugini V, Guildford A L & Santin M (2011). Synthesis, Characterisation and in vitro Anti-Angiogenic Potential of Dendron VEGF Blockers. Macromolecular Bioscience, 11, 1761-1765.

Shin J, Kim Y-M, Li S-Z, Lim S-K & Lee W (2008). Structure-Function of the TNF Receptor-like Cysteine-rich Domain of Osteoprotegerin. Molecules and Cells, 25, 352-357.

Ta H M, Nguyen G, Thi, Tuyet, Jin H, Mi, Choi J, Park H, Kim N, Hwang H-Y & Kim K, Kyu (2010). Structure-Based Development of a Receptor Activator of Nuclear Factor-kB Ligand (RANKL) Inhibitor Peptide and Molecular Basis for Osteoporosis Proceedings of the National Academy of Sciences of the United States of America, 107, 20281-20286.

Viola-Villegas N & Doyle R P (2009). The coordination chemistry of 1,4,7,10-tetraazacyclododecane-N,N',N'', N'''-tetraacetic acid (H4DOTA): Structural overview and analyses on structure-stability relationships. Coordination Chemistry Reviews, 253, 1906-1925.

Xiangyang X, Ling L, Jianping Z, Shiyue L, Jie Y, Xiaojin Y & Jinsheng R (2007). Preparation and characterization of N-succinyl-N'-octyl chitosan micelles as doxorubicin carriers for effective anti-tumor activity. Colloids and Surfaces B: Biointerfaces, 55, 222-228.

Yan C, Chen D, Gu J, Hu H, Zhao X & Qiao M (2006). Preparation of N-succinyl-chitosan and its physical-chemical properties as a novel excipient. Yakugaku Zasshi, 126, 789-793.

The invention claimed is:

1. A bone biospecific agent comprising a contrast material core, which is visible using Magnetic Resonance Imaging (MRI) or Computed Tomography (CT), the contrast material core being optionally surrounded by a polymeric shell, wherein the core or polymeric shell is functionalised with a bone-targeting peptide, wherein the peptide, in use, targets the biospecific agent to bone, and wherein the peptide mimics proteins participating in the inhibition of osteoclast-osteoclast and/or osteoclast-osteoblast interactions, or recognises the mineral phase of bone,
wherein the bone targeting peptide comprises:
   (i) a peptide selected from SEQ ID Nos: 1 to 8 conjugated to a peptide selected from SEQ ID Nos: 9-11, and 1,4,7,10-tetraazacyclododecane-1,4,7,10-tetraacetic acid (DOTA),
   (ii) a peptide of SEQ ID No: 12 and 1,4,7,10-tetraazacyclododecane-1,4,7,10-tetraacetic acid (DOTA), or
   (iii) a peptide selected from SEQ ID Nos: 13-14, and
wherein the contrast material core comprises a non-magnetic material.

2. A biospecific agent according to claim 1, wherein the contrast material core is both an MM and a CT contrast material.

3. A biospecific agent according to claim 1, wherein the contrast material core comprises gadolinium, gold, iodine or boro-sulphate.

4. A biospecific agent according to claim 1, wherein the contrast material core comprises gadolinium.

5. A biospecific agent according to claim 1, wherein the contrast material core is gadolinium and the bone-targeting peptide is covalently bonded to the core.

6. A biospecific agent according to claim 1, wherein the polymeric shell is functionalised with one, two or more species of bone-targeting peptide, which target the biospecific agent to bone.

7. A biospecific agent according to claim 1, wherein the bone-targeting peptide targets the biospecific agent to: (i) a cell present exclusively in bone and selected from a group consisting of an osteoblast, osteocyte, osteoclast, bone cell progenitor, osteoclast progenitor and a bone lining cell; or (ii) to the bone mineral phase or hydroxyapatite.

8. A biospecific agent according to claim 1, wherein the bone-targeting peptide is attached to the polymeric shell of the bone biospecific agent by covalent bonding.

9. A biospecific agent according to claim 1, wherein the biospecific agent comprises a bioactive compound, which is delivered to the bone due to the presence of the bone-targeting peptide.

10. A biospecific agent according to claim 9, wherein the bioactive compound is selected from a group of molecules consisting of: a dye, electrochemical mediator, protein, peptide, chemical compound, a drug, genetic material, an oligonucleotide, DNA, RNA, small molecule, antibody, and an enzyme.

11. A biospecific agent according to claim 1, wherein the mean diameter of the biospecific agent is 100-450 nm.

12. A biolabel comprising the bone biospecific agent according to claim 1.

13. A pharmaceutical composition comprising the bone biospecific agent according to claim 1, and a pharmaceutically acceptable vehicle.

14. A biospecific agent according to claim 1, wherein the bone-targeting peptide is attached to the polymeric shell of the bone biospecific agent by carbodiimide chemistry.

15. A biospecific agent according to claim 1, wherein the polymeric shell comprises a biocompatible natural or synthetic polymer including chitosan, collagen, gelatine, hyaluronic acid, poly(ethylene glycol) poly(lactic acid), poly(glycolic acid), poly(epsilon-caprolactone) or poly(acrylic acid).

16. A biospecific agent according to claim 1, wherein the polymeric shell is derivatised with succinic anhydride.

* * * * *

SEQUENCE LISTING

<160> NUMBER OF SEQ ID NOS: 15

<210> SEQ ID NO 1
<211> LENGTH: 11
<212> TYPE: PRT
<213> ORGANISM: Homo sapiens

<400> SEQUENCE: 1

Ser Arg Pro Thr Glu Lys Thr Ile Phe Ile Ile
1               5                   10

<210> SEQ ID NO 2
<211> LENGTH: 9
<212> TYPE: PRT
<213> ORGANISM: Homo sapiens

<400> SEQUENCE: 2

Tyr Cys Leu Glu Ile Glu Phe Cys Tyr
1               5

<210> SEQ ID NO 3
<211> LENGTH: 11
<212> TYPE: PRT

```
<213> ORGANISM: Homo sapiens

<400> SEQUENCE: 3

Tyr Cys Glu Ile Glu Phe Cys Tyr Leu Ile Arg
1               5                   10

<210> SEQ ID NO 4
<211> LENGTH: 7
<212> TYPE: PRT
<213> ORGANISM: Homo sapiens

<400> SEQUENCE: 4

Phe His Arg Arg Ile Lys Ala
1               5

<210> SEQ ID NO 5
<211> LENGTH: 5
<212> TYPE: PRT
<213> ORGANISM: Homo sapiens

<400> SEQUENCE: 5

Pro Ser His Arg Asn
1               5

<210> SEQ ID NO 6
<211> LENGTH: 5
<212> TYPE: PRT
<213> ORGANISM: Homo sapiens

<400> SEQUENCE: 6

Tyr Ile Gly Ser Arg
1               5

<210> SEQ ID NO 7
<211> LENGTH: 12
<212> TYPE: PRT
<213> ORGANISM: Homo sapiens

<400> SEQUENCE: 7

Ser Thr Leu Pro Ile Pro His Glu Phe Ser Arg Glu
1               5                   10

<210> SEQ ID NO 8
<211> LENGTH: 12
<212> TYPE: PRT
<213> ORGANISM: Homo sapiens

<400> SEQUENCE: 8

Val Thr Lys His Leu Asn Gln Ile Ser Gln Ser Tyr
1               5                   10

<210> SEQ ID NO 9
<211> LENGTH: 3
<212> TYPE: PRT
<213> ORGANISM: Homo sapiens

<400> SEQUENCE: 9

Lys Lys Lys

<210> SEQ ID NO 10
<211> LENGTH: 7
<212> TYPE: PRT
<213> ORGANISM: Homo sapiens

<400> SEQUENCE: 10
```

```
Lys Lys Lys Lys Lys Lys Lys
1               5

<210> SEQ ID NO 11
<211> LENGTH: 15
<212> TYPE: PRT
<213> ORGANISM: Homo sapiens

<400> SEQUENCE: 11

Lys Lys Lys Lys Lys Lys Lys Lys Lys Lys Lys Lys Lys Lys Lys
1               5                   10                  15

<210> SEQ ID NO 12
<211> LENGTH: 16
<212> TYPE: PRT
<213> ORGANISM: Homo sapiens

<400> SEQUENCE: 12

Lys Lys Lys Lys Lys Lys Lys Tyr Cys Leu Glu Ile Glu Phe Cys Tyr
1               5                   10                  15

<210> SEQ ID NO 13
<211> LENGTH: 15
<212> TYPE: PRT
<213> ORGANISM: Homo sapiens
<220> FEATURE:
<221> NAME/KEY: MOD_RES
<222> LOCATION: (1)
<223> OTHER INFORMATION: DOTA is bound to the Lys.

<400> SEQUENCE: 13

Lys Gly Gly Tyr Cys Leu Glu Ile Glu Phe Cys Tyr Leu Ile Arg
1               5                   10                  15

<210> SEQ ID NO 14
<211> LENGTH: 15
<212> TYPE: PRT
<213> ORGANISM: Homo sapiens
<220> FEATURE:
<221> NAME/KEY: MOD_RES
<222> LOCATION: (1)
<223> OTHER INFORMATION: Gadoteric acid, which comprises DOTA and
      gadolinium (Gd3+), is bound to Lys.

<400> SEQUENCE: 14

Lys Gly Gly Tyr Cys Leu Glu Ile Glu Phe Cys Tyr Leu Ile Arg
1               5                   10                  15

<210> SEQ ID NO 15
<211> LENGTH: 7
<212> TYPE: PRT
<213> ORGANISM: Homo sapiens
<220> FEATURE:
<221> NAME/KEY: MOD_RES
<222> LOCATION: (1)
<223> OTHER INFORMATION: Gadoteric acid, which comprises DOTA and
      gadolinium (Gd3+), is bound to the Phe.

<400> SEQUENCE: 15

Phe His Arg Arg Ile Lys Ala
1               5
```